(12) United States Patent
Knutson et al.

(10) Patent No.: US 8,169,600 B2
(45) Date of Patent: May 1, 2012

(54) SURFACE MAPPING BY OPTICAL MANIPULATION OF PARTICLES IN RELATION TO A FUNCTIONALIZED SURFACE

(75) Inventors: Christopher Knutson, Chicago, IL (US); Crystal Duke, Stanford, CA (US); Gary Stacey, Marshfield, MA (US); Dan Mueth, Chicago, IL (US); Evan Tanner, La Jolla, CA (US); Osman Akcakir, Chicago, IL (US); Haojun Fu, Naperville, IL (US); Robert Lancelot, Barrington, IL (US); Tania Chakrabarty, Chicago, IL (US); Kenneth Bradley, Hinsdale, IL (US)

(73) Assignee: Arryx, Inc., Chicago, IL (US)

( * ) Notice: Subject to any disclaimer, the term of this patent is extended or adjusted under 35 U.S.C. 154(b) by 373 days.

(21) Appl. No.: 12/440,949

(22) PCT Filed: Sep. 14, 2007

(86) PCT No.: PCT/US2007/078561
§ 371 (c)(1),
(2), (4) Date: Nov. 5, 2009

(87) PCT Pub. No.: WO2008/034102
PCT Pub. Date: Mar. 20, 2008

(65) Prior Publication Data
US 2011/0026009 A1  Feb. 3, 2011

Related U.S. Application Data

(60) Provisional application No. 60/844,911, filed on Sep. 15, 2006, provisional application No. 60/844,890, filed on Sep. 15, 2006, provisional application No. 60/844,910, filed on Sep. 15, 2006, provisional application No. 60/844,763, filed on Sep. 15, 2006, provisional application No. 60/931,451, filed on May 22, 2007.

(51) Int. Cl.
*G01N 33/48*  (2006.01)
(52) U.S. Cl. .......................................................... 356/39
(58) Field of Classification Search ..................... 356/39, 356/601
See application file for complete search history.

(56) References Cited

U.S. PATENT DOCUMENTS 5,100,627 A   3/1992   Buican et al. .................. 422/108
(Continued)

FOREIGN PATENT DOCUMENTS

WO        WO 00/61198        10/2000
(Continued)

OTHER PUBLICATIONS

European Patent Office, Authorized officer: Wolfgang-Peter Schießl *Notification of Transmittal of the International Search Report and The Written Opinion of the International Searching Authority, or The Declaration*, PCT/US2007/078561, dated Apr. 21, 2008, 11 pages.

(Continued)

*Primary Examiner* — Roy M Punnoose
(74) *Attorney, Agent, or Firm* — Sunstein Kann Murphy & Timbers LLP

(57) ABSTRACT

Methods and apparatus for analyzing surface properties of particles are provided. A method for analyzing the surface properties of the particle includes a associating a first particle with a first capture zone having a specific binding affinity for a first chemical species, applying an optical force to the first particle, sensing a response of the first particle to the optical force, and using the sensed response to determine the presence, absence or quantity of the first chemical species on the first particle surface. This process may be repeated in parallel to test multiple particles. In addition to directly testing the surface properties of the particles, the method can be used in direct, indirect and competitive assays to determine the presence, absence or quantity of free or immobilized analytes. A fluidic cartridge with capture zones having avidities that are tuned for the use of optical forces is provided. A software routine for performing the method is also provided.

20 Claims, 22 Drawing Sheets

U.S. PATENT DOCUMENTS

| | | | |
|---|---|---|---|
| 5,147,606 A | 9/1992 | Charlton et al. | 422/56 |
| 5,198,369 A | 3/1993 | Itoh et al. | 436/534 |
| 5,304,487 A | 4/1994 | Wilding et al. | 435/291 |
| 5,571,410 A | 11/1996 | Swedberg et al. | 210/198.2 |
| 5,620,857 A | 4/1997 | Weetall et al. | 435/7.1 |
| 5,800,690 A | 9/1998 | Chow et al. | 204/451 |
| 5,837,115 A | 11/1998 | Austin et al. | 204/450 |
| 6,139,831 A | 10/2000 | Shivashankar et al. | 424/82.05 |
| 6,159,749 A | 12/2000 | Liu | 436/527 |
| 6,251,615 B1 | 6/2001 | Oberhardt | 435/7.21 |
| 6,368,871 B1 | 4/2002 | Christel et al. | 436/180 |
| 6,387,707 B1 | 5/2002 | Seul et al. | 436/164 |
| 6,416,190 B1 | 7/2002 | Grier et al. | 359/614 |
| 6,815,664 B2 | 11/2004 | Wang et al. | 250/251 |
| 6,833,542 B2 | 12/2004 | Wang et al. | 250/251 |
| 6,966,880 B2 | 11/2005 | Boecker et al. | 600/583 |
| 6,991,906 B1 | 1/2006 | Fuhr et al. | 435/7.1 |
| 7,049,579 B2 | 5/2006 | Ozkan et al. | 250/251 |
| 7,068,874 B2 | 6/2006 | Wang et al. | 385/16 |
| 7,079,241 B2 | 7/2006 | Empedocles et al. | 356/326 |
| 7,104,659 B2 | 9/2006 | Grier et al. | 359/614 |
| 7,150,834 B2 | 12/2006 | Mueth et al. | 210/732 |
| 2002/0160470 A1 | 10/2002 | Zhang | 435/173.1 |
| 2003/0119177 A1 | 6/2003 | Gruber et al. | 435/287.2 |
| 2004/0180363 A1 | 9/2004 | Gruber et al. | 435/6 |
| 2005/0136412 A1 | 6/2005 | Gingeras | 435/6 |
| 2006/0134603 A1 | 6/2006 | Plewa et al. | 435/4 |
| 2008/0290037 A1 | 11/2008 | Liu | 210/695 |
| 2009/0075826 A1 | 3/2009 | Chakrabarty | 506/6 |
| 2010/0178656 A1* | 7/2010 | Buffiere et al. | 435/7.1 |

FOREIGN PATENT DOCUMENTS

| | | |
|---|---|---|
| WO | WO 03/001178 | 1/2003 |

OTHER PUBLICATIONS

Bockelmann et al. "*Unzipping DNA with Optical Tweezers: High Sequence Sensitivity and Force Flips*", Biophysical Journal, vol. 82, No. 3, pp. 1537-1553, Mar. 2002.

Zlatanova et al. "*Stretching and imaging single DNA molecules and chromatin*", Journal of Muscle Research and Cell Motility, vol. 23, No. 5-6, pp. 377-395, 2002.

Holmlin, et al. "*Light-Driven Microfabrication: Assembly of Multicomponent, Three-Dimensional Structures by Using Optical Tweezers \*\**", Angew. Chem. Int. Ed. 2000, vol. 39, No. 19, pp. 3503-3506.

Arryx, Inc. "*BioRyx 200® Applications, Enabling A New Generation of Research*", Brochure, 2000.

Helmerson, et al. "*Optical tweezers-based immunosensor detects femtomolar concentrations of antigens*", Clinical Chemistry, vol. 43, No. 2, pp. 379-383, 1997.

Wei et al. "*Mapping the sensitivity of T cells with an optical trap: Polarity and minimal number of receptor of $Ca^{2+}$ signaling*", Proc. Natl. Acad., Sci., USA, vol. 96, pp. 8471-8476, Jul. 1999.

Mammen, et al. "*Optically controlled collisions of biological objects to evaluate potent polyvalent inhibitors of virus-cell adhesion*", Chemistry and Biology, vol. 3, No. 9, pp. 757-763, 1996.

"*Optical Tweezers and Immunoassay*", Editorial, Clinical Chemistry, vol. 43, No. 2, pp. 251-253, 1997.

European Patent Office, Authorized Officer: Atashi, Shara, *Invitation to Pay Additional Fees and Where Applicable, Protest Fee*, PCT/US2010/08332, mailed Nov. 10, 2010, 6 pages.

\* cited by examiner

SURFACE MAPPING BY OPTICAL MANIPULATION OF PARTICLES IN RELATION TO A FUNCTIONALIZED SURFACE

CROSS REFERENCE TO RELATED APPLICATIONS

This patent application claims priority from U.S. Provisional Patent Application Ser. No. 60/844,911 for "Determination of antigen-antibody attachment for protein assay and blood typing by manipulation of multiple bodies within an optically defined potential" filed 15 Sep. 2006; U.S. Provisional Patent Application Ser. No. 60/844,890 for "Substrate Functionalization for Blood Typing" filed 15 Sep. 2006; U.S. Provisional Patent Application Ser. No. 60/844,910 for "Analytical cartridge for optical manipulation" filed on 15 Sep. 2006; U.S. Provisional Patent Application Ser. No 60/844,763 for "Compact sample testing apparatus incorporating holographic optical trapping" filed 15 Sep. 2006; and U.S. Provisional Patent Application Serial No. 60/931,451 for "Analytical cartridge for blood typing" filed May 22, 2007. All of the aforementioned Provisional Patent Applications are hereby incorporated by reference herein in their entirety.

TECHNICAL FIELD

The present invention relates to the use of optically generated forces to manipulate analyte or probe particles for the purpose of analysis, including cell-surface antigen analysis.

BACKGROUND

The use of arrayed molecules in formats such as microplates and biochips allows an ever increasing amount of information to be retrieved about the natural world. Although many variants are known, use of such arrays typically involves immobilizing probes or analytes on a substrate and using a variety of techniques to measure the interaction of the immobilized molecules with other, solution-phase, molecules. Specific examples of such array techniques include immunoassays (e.g., enzyme-linked immunoassays, ELISAs) that are performed in microplates, nucleic acid biochips (e.g., those commercialized by Affymetrix and Illumina) and protein biochips (e.g., the Invitrogen ProtoArray™). Biochips most commonly utilize glass substrates, while microplates for ELISA are often constructed from gamma-irradiated polystyrene. Although arrays are typically ordered, in the sense that immobilized molecules are placed at defined locations with respect to each other or to reference features, so-called "solution-phase arrays" have also been commercialized. The Luminex X-Map™ technology measures binding of analytes to a suspension of beads. The suspension is created by mixing batches of particles that are co-labeled with binding probes and corresponding mixtures of two fluorescent identifier molecules in varying ratios. Bound fluorescently labeled analyte is detected along with the identifier ratios using a flow cytometer.

In addition to the detection of individual molecules, particles (including biological cells) have been analyzed using array techniques. For example, it is known in the art to detect cell surface antigens through ELISA or flow cytometry. U.S. Pat. No. 6,251,615 to Oberhardt discloses testing cells using microscopy to detect cells bound to one of a plurality of capture zones with coupled antibody receptors.

A major limitation for conventional arrays is that long incubation times are usually required to reach a state of binding that is sufficiently close to equilibrium to allow useful analysis. This may entail allowing samples or reagents to incubate in an ELISA microplate or biochip for many hours, and in some cases, longer than a typical business day of 8 hours. Such delays can cause added expense, preclude use in emergency situations, and reduce data quality due to degradation of reagents during the protracted incubation times. Other limitations of conventional approaches is the need for analyte labeling steps and stringent washing steps, which introduce additional costs in terms of labor and equipment, and may impact data quality. Microplate based approaches use relatively large volumes of test samples and reagents.

As is known in the art, red blood cells ("RBCs") from different patients may have different antigens on their surfaces, and transfusion of whole blood from a patient having certain RBC antigens to another patient that lacks those antigens may cause a deleterious immune reaction in the blood recipient. Therefore, blood typing is performed, typically by agglutination assay Blood typing entails the identification of blood group antigens or antibodies as present on the surface of a subject's RBCs. Blood group A and B antigens are typically identified, as are various antigens associated with the Rh system, of which the D antigen is clinically the most critical. Currently, blood typing is performed by detecting the agglutination of red blood cells (RBC's) upon the addition of blood group antibodies (see, for example, U.S. Pat. No. 4,894,347 to Hillyard, et. al.). Agglutination of a blood sample indicates a positive result for an antigen matching the antibody added (for example, blood group antigen A, blood type antigen Rh).

Due to the variation in antibody reactivity from person to person, and due to possible prior existence of antibodies within a subject's blood, the potential exists for spurious results. A false result leads to incorrect blood typing, which can result, in turn, in the possibility of an adverse transfusion reaction. Moreover, current technologies require a relatively large amount of blood (~3 mL) for testing. Therefore the ability to type blood while utilizing a smaller volume would increase donor comfort and be of great use when dealing with anemic patients such as newborns suffering from Hemolytic Disease of the Newborn (HDN). The ability to type blood from a single sample would also be a significant improvement over existing technology which currently used a blood sample that is separately inputted into multiple individual reaction volumes for every antigen tested.

Furthermore, the capacity to gauge the parallel interaction of small numbers of RBCs, or of other cells or more general organic bodies, with respect to a variety of reagents each having a known specific affinity for a particular analyte, would be of great analytical and diagnostic value. The parallel assaying of RBCs from a single blood sample with respect to antigens of both the ABO and Rh systems is an example of one application of such a system.

Holographic optical trapping (HOT) provides a useful tool for manipulation of microscopic and nanoscopic particles such as biological components. The basic principals of holographic optical trapping as well as systems configured to create and use such optical traps are disclosed in U.S. Pat. No. 6,055,106, U.S. patent application Ser. Nos. 10/701,324, and 09/886,802, the entirety of which are incorporated herein by reference.

In examining small sample particles in a microscope-based system, it is necessary to place the sample in a fluidic cartridge, such as a microscope slide so that it can be held in alignment with the optics of the microscope system. Such a fluidic cartridge may also be known as a sample slide, sample chip or cover slip. Sample slides useful in holographic optical trapping techniques are disclosed in U.S. patent application Ser. No. 10/294,599, U.S. Patent Publication No. 20030119177, the entirety of which is incorporated herein by reference.

SUMMARY OF THE INVENTION

In accordance with illustrative embodiments of the invention, a method is used for analyzing surface properties of one or more particles each having a surface. The method comprises introducing a suspension having a plurality of particles into a sample holder having at least one capture zone with a given affinity for a chemical species, contacting at least a subset of the plurality of the particles with the at least one capture zone so as to allow for binding interactions to occur between the at least one capture zone and the at least a subset of particles, the binding interactions being related to the surface composition of the particles, applying optical forces to at least two of the at least a subset of particles concurrently, the forces tending to cause a response of the particles, wherein the responses depend on the presence, absence or degree of binding interactions between the particles and the at least one capture zone, sensing the responses of the at least two particles to the optical forces, and using the sensed responses to determine the composition of the surfaces of the particles.

The applying optical forces may include using holographic optical tweezers (HOT). The contacting may include contacting multiple particles with a single capture zone, and sensing the responses of the multiple particles to optical forces. The method may include contacting a first particle with a first capture zone having a specific binding affinity for a first chemical species so as to allow for a binding interaction to occur between the first capture zone and the first particle, the binding interaction being related to the presence of molecules of the first chemical species on the surface of the first particle, contacting a second particle with a second capture zone having a specific binding affinity for a second chemical species so as to allow for a binding interaction to occur between the second capture zone and the second particle, the binding interaction being related to the presence of molecules of the second chemical species on the surface of the second particle, applying an optical force to the first and second particles, the forces tending to cause responses of the particles, sensing the response of the first and second particles to the optical forces, using the sensed responses to determine the presence, absence or quantity of the first chemical species on the first particle surface and of the second chemical species on the second particle surface.

The method may include identifying particles prior to applying forces to the particles. The method may also include identifying particles, selecting a first group of identified particles, applying optical forces to the first group of particles, selecting a second group of particles, and applying optical forces to the second group of particles.

The steps of the method may be repeated to reach a data acquisition threshold.

The force may have a component normal to and oriented away from the capture zone. Alternately or in addition, the force may have a component parallel to a plane defined by the capture zone. The force may tend to displace unbound particles to a position that is spaced from the capture zone in both a first direction that is normal to and a second direction that is parallel to a plane defined by the capture zone.

The response may include dislodging of the particle from the capture zone.

The particle may be a cell. The chemical species may be a cell surface antigen.

In an embodiment, the particle is a red blood cell and at least one capture zone includes a cell-surface antigen-specific probe. Additionally, the determination may be used to further determine a blood type, including a blood type involving three or more surface antigens, for example, a minor blood type.

The probe may be, for example, antibody, an antibody fragment, or an aptamer. The contacting step may include allowing the particle to settle through a solution, e.g., using gravitational forces to cause the particle to settle or using optical forces to cause the particle to settle. The contacting may also include introducing a solution to a volume defined in part by the first surface and in part by a cover spaced apart from the first surface, at least one of the surface and the cover being substantially optically transparent. The cover maybe spaced apart from the first surface by a distance of more than one times and less than 1000 times a diameter of the first particle. The cover may be spaced apart from the first surface by a distance of more than two times and less than twenty times a diameter of the first particle. The cover may be spaced apart from the first surface by a distance in the range of 15 microns to 500 microns. The cover is spaced apart from the surface by a distance that is sufficiently large so as to disfavor clogging of the space defined by the first surface and the cover yet sufficiently small so as to permit the first particle to settle in less than 10 minutes. The step of applying an optical force comprises using holographic optical tweezers.

The first capture zone may include a plurality of probe molecules having a specificity for a first target moiety, the probe molecules being configured so as to have an avidity for a particle having multiple first target moieties thereon, the configuration of the probe molecules being selected to allow dislodging by a force within a specified range. The specified range may be, for example, 1 to 1000 pN, 10 to 200 pN or 20 to 100 pN. The method may also include a second capture zone includes a plurality of probe molecules having a specificity for a second target moiety, the probe molecules being configured on the surface so as to have an avidity for a particle having multiple second target moieties thereon, the configuration of the probe molecules being selected to allow dislodging by a force in the specified range. The specified range may be, for example, 1 to 1000 pN, 10 to 200 pN or 20 to 100 pN. The probe molecules of a capture zone are configured for dislodging in the specified range by altering the length of a linker moiety that connects the surface and the probe. The probe molecules of a capture zone may also be configured for dislodging in the specified range by altering the areal density of the probes. The method may use using non-binding surface moieties to space-apart the probes so as to achieve the first and second avidities. A cell surface may be characterized by choosing the areal density based on an expected density of cell surface antigens on the cell surface.

Applying the optical force may include centering an optical trap at a distance from a particle, the potential energy of the particle being substantial at the surface and at a minimum at the center of the optical trap, so that if the particle is dislodged from the surface by the optical force of the trap, the particle will travel to the center of the optical trap.

The contacting may include introducing the first particle in a solution by passive flow.

The method may include varying the magnitude of the optical force applied to a particle so as to increase the magnitude of the force with time and recording the amount of force required to dislodge the particle from the surface. The method may include comparing the recorded force to a reference force to determine the presence, absence or quantity of the first chemical species on the first particle surface. The sensing may include using automated microscopy. The application of optical force may be automated.

A sample holder may be used to perform an operation selected from diluting and filtering the sample prior to analysis.

In accordance with an embodiment of the present invention, a method is used for determining the presence, absence, or quantity of multiple blood cell surface antigens in a blood sample of a patient. The method includes diluting a blood sample, contacting the diluted blood sample with first and second capture zones, the first zone functionalized to have a specific affinity for a first blood cell antigen and the second zone functionalized to have a specific affinity for a second blood cell antigen, applying a first optical force having a dislodging component to at least one cell in the first zone, the first force being sized to be sufficient to dislodge a cell from the first zone if the first blood cell antigen is not present on the cell yet insufficient to dislodge a cell on which the first blood cell antigen is present, applying a second optical force having a dislodging component to at least one cell in the second zone, the second force being sized to be sufficient to dislodge a cell from the second zone if the second blood cell antigen is not present on the cell yet insufficient to dislodge a cell on which the second blood cell antigen is present, and detecting dislodgement or non-dislodgment of the cells from the zones. The contacting may further comprise allowing the cells to settle under the force of gravity.

In accordance with an embodiment of the present invention, an apparatus for the analysis of the presence, absence or quantity of target moieties on one or more particles includes a substrate a first and second capture zone disposed on the substrate, each capture zone comprising a plurality of probe moieties, wherein the avidity of the first and second capture zones are configured so that particles having a higher affinity to the capture zones will tend to be retained in the presence of a displacing optical force and particles having a lesser affinity for the capture zones will tend to be displaced in the presence of a displacing optical force, the optical force being in a specified range.

Optionally, the apparatus may include a cover, wherein at least one of the base, capture zone and cover being optically transparent, an inlet and an outlet from a volume defined by the capture zone and the cover, a spacer for spacing the cover from the capture zone and sized so that a upon introduction of a solution containing mammalian cells, a majority of the cells will settle to the capture zones within 5 minutes or less. The spacer is also sized to allow introduction of the solution to the volume defined by the capture zone and the cover via passive flow.

The apparatus may include a cover is optically transparent to infrared light. The specified range for the apparatus may be, e.g., 1 to 1000 pN, 10 to 200 pN, or 20 to 100 pN. The apparatus may be configured for blood typing and may also be operable to perform a sample handling procedure selected from diluting and filtering the sample.

In accordance with an embodiment of the present invention a method includes cleaving an IgM solution into a solution of fragments containing multiple antigen-binding domains, further cleaving the binding domains into antigen-binding sub-fragments, and attaching the sub-fragments to a substrate to create a capture zone for specific binding recognition of a first antigen. The method may also include creating a second capture zone for specific binding recognition of a second antigen. The method may include exposing like particles to the first and second capture zones and ranking the affinity of the particle to the regions to identify a common antigen present on the particle surface. The particle may be a cell. Ranking the affinity may include applying an optical force to the particle. The force may be simultaneously applied to a second particle. The forces may be applied using HOT.

In accordance with an embodiment, there is a method for determining the presence, absence or quantity of a plurality of molecules in a solution that includes providing a substrate with at least a first capture zone with a first immobilized probe, and a second capture zone with a second immobilized probe, contacting the capture zones with an analyte solution under conditions sufficient to allow binding of analyte molecules to the probes, contacting the bound analyte with a particle having an immobilized universal probe that specifically binds to multiple species of bound analyte molecules, applying an optical force to the particle, and observing a response of the particle to the optical force that is dependent on the binding between the universal probe and the bound analyte.

Optionally or in addition, the method may include contacting the bound analyte with a plurality of particles, applying optical forces to the particles, and observing the response of the particles. The application of forces to the particles may be performed concurrently. The analyte solution may contact multiple capture zones in a manner so as to cause fluid communication to be established among the capture zones. Alternately, or in addition, the analyte solution may contact multiple capture zones without allowing fluid communication between capture zones. The analyte solution may include patient antibodies. The universal probe may include secondary antibodies with a broad selectivity for at least a class of the patient antibodies. The class of antibodies may be selected from one of IgG, IgE, IgA, and IgM.

In accordance with an embodiment of the present invention, a computer program product on a tangible computer readable medium for use with a computer system includes computer code for identifying a plurality of particles of interest in contact with a capture zone, computer code for actuating an application of a displacing optical forces to the particles, and computer code for recording observed responses of the particles to the optical forces.

Optional or in addition, the computer program product may include computer code for selecting a plurality of microscopic fields, and/or computer code for determining when a threshold quantity of data has been accumulated.

In accordance with an embodiment of the invention, a method for the analysis of the surface properties of a plurality of particles includes introducing a suspending containing the plurality of particles into a fluidic cartridge having a plurality of capture zones on a substrate, the cartridge defining liquid column bounded by a cover, allowing the particles to settle so as to contact the capture zones, applying optical forces to the particles; and observing responses of the particles to the optical forces. The height of the liquid column is chosen to allow a red blood cell to settle to contact the capture zone in a time period of less than 10 minutes, or less than 5 minutes.

In accordance with embodiment of the present invention, a method for competitive assay includes creating a plurality of sandwich structures, each sandwich structure comprising a collection of first probe molecules that are immobilized to a substrate, a collection of placeholder molecules that are reversibly bound to the first prove molecules and a particle bearing a plurality of second probe molecules that are reversibly bound to the placeholder molecules, adding an analyte solution, incubating for a time sufficient to allow analyte molecules having affinity for the first and second probe molecules to displace at least some of the placeholder molecules so as to alter the binding strength between the particles and the substrate, applying optical forces to the particles, observing responses of the particles to the optical forces and using the responses to determine the contents of the analyte solution.

The sandwich structures may be specific for different corresponding analyte molecules are placed at different regions of the substrate so as to report on a plurality of analyte species. The placeholder molecules may tend to create a stronger binding force between the particle and the substrate than do corresponding analyte molecules. Alternately, or in addition, placeholder molecules may tend to create a weaker binding force between the particle and the substrate than do corresponding analyte molecules. The optical forces may be applied to a plurality of particles concurrently.

In accordance with embodiment of the invention, a component sample handling system employs HOT capability and a microscope and includes an enclosure, a sample stage with a sample area, a HOT subsystem that includes a laser, a diffractive optical element, a HOT emission port directed at the sample area, at least one illumination source with a source output directed at the sample area, an objective lens optically alignable with the sample area, a camera arranged to be focused on the sample area. At least the sample area, HOT emission port, and illumination source output are enclosed in the enclosure.

Optionally, or in addition, all the components are carried on a mobile structure. The system may also include at least one feature selected from the group consisting of an integral computer interface, a safety mechanism for turning off laser illumination in response to a lid opening, a jig for positioning a fluidic sample cartridge, and a wheeled mounting.

BRIEF DESCRIPTION OF THE DRAWINGS

The foregoing features of the invention will be more readily understood by reference to the following detailed description, taken with reference to the accompanying drawings, in which:

FIG. 23a is a schematic of the assay of FIG. 23a in which the antigen is not recognized by the complex;

DETAILED DESCRIPTION OF SPECIFIC EMBODIMENTS

Figure 3:
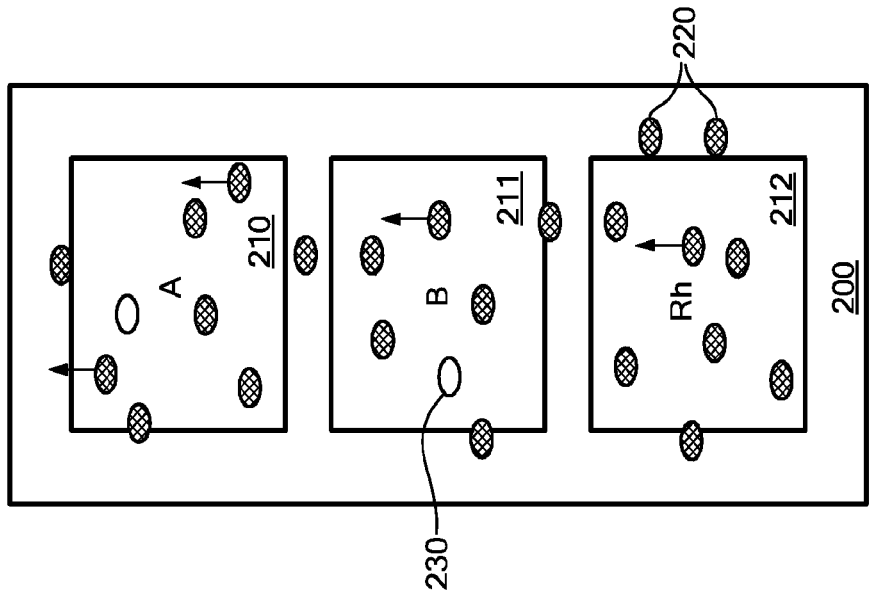
FIG. 3 shows the apparatus of FIG. 2 with blood cells to be analyzed.

Definitions. As used in this description and the accompanying claims, the following terms shall have the meanings indicated, unless the context otherwise requires:

An "optical force" shall mean a force exerted on a particle using a suitably directed or patterned illumination so as to create a state of elevated potential energy tending to displaced the particle in a given direction.

A "particle" shall mean an object that has a surface and is capable of being manipulated by an optical force. Cells and viruses are "particles", as are small polymeric and inorganic objects, such as microspheres or microbeads of various shapes and compositions.

In connection with a particle, a "surface" shall mean that portion of the particle that is accessible to a probe.

In connection with a fluidic cartridge or other sample holder, "passive flow" shall mean that the sample holder draws fluid by capillary action or other means, without the use of a pump.

As it relates to an instrument for particle analysis, the term "automated microscopy" shall mean that through appropriate positioning and/or software routines, the instrument at least automatically locates particles for analysis and records their positions.

As it relates to entities on the surface of a particle, a "chemical species" shall mean any molecule, molecular assembly, macromolecule, macromolecular assembly or moiety. The term "chemical species" expressly includes biological and non-biological macromolecules such as peptides, proteins, carbohydrates, glycoproteins, antibodies, nucleic acids, polymers, drug complexes, and the like.

A "probe" means a molecular entity, particle, or assembly of molecular entities that has a specific binding preference for a given target particle, molecule, assembly, or moiety.

A "capture zone" shall mean a surface region that includes receptors to render it capable of specifically interacting with a given analyte.

An "array," as used herein and in any appended claims, refers to a plurality of elements of a set disposed at discrete spatial positions, whether at one or multiple instances of time, and whether regularly spaced, periodically spaced, or otherwise.

A "blood type" includes determination of any individual or combination of antigens selected from: A, B, Rh (including all 53 Rh antigens Rh1 through Rh53 as defined by the International Society Blood Transfusion), $A_3$, $A_x$, $A_{end}$, $A_m$, $A_y$, $A_{el}$, $B_3$, $B_x$, $B_m$, $B_{el}$, Duffy, Kell, Kidd, Lewis, MNSs, Lutheran, Diego, Cartwright, Xg, Scianna, Dombrock, Colton, Landsteiner-Weiner, Chido-Rodgers, H, Kx, Gerbich, Cromer, Knops, Indian, Ok, Raph, John Milton Hagen, I, Globoside, GIL and other blood type antigens.

Illustrative embodiments of the present invention relate to methods and apparatus for observing interactions between particle surfaces and other surfaces for purposes of extracting information related to the propensity of the surfaces to interact and using this information to reach conclusions regarding the composition of the surfaces, analytes that interact with the surfaces, or other properties of an analyte sample. The interactions may be probed by exerting targeted optical forces upon a plurality particles, including cells, for the purposes of testing their ability to interact with molecular recognition elements. By using parallel optical trapping or optical tweezing techniques, such testing may be performed in a rapid, cost-effective manner to yield a wealth of high-quality measurements. Embodiments also relate to apparatus and methods that employ automated instruments to apply forces to the particles in a parallel manner and to sense responses to the applied forces. Aspects of the invention are applicable to, among others, biological and biochemical analyses including analysis of cell surface antigens (e.g., blood typing and cancer or other disease-state diagnostics), the analysis of antibodies or other biomarkers characteristic of disease states, and for the analysis of proteins using arrayed antibodies on a protein chip. A specific embodiment of the invention relates to using a thin, transparent chamber to analyze particles. Because the chamber is thin, the particles can be made to contact a capture zone much faster than is typically achieved in conventional affinity bioassays.

Figure 1:
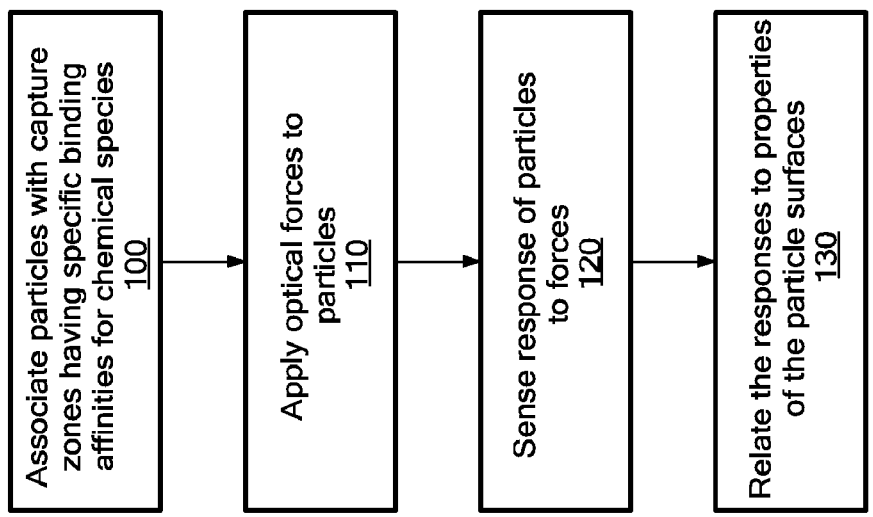
FIG. 1 a flow-chart of a method for analysis of a particle surface in accordance with an embodiment of the invention.

FIG. 1 is a flow diagram of a method for characterization of surface properties of a particle in accordance with an embodiment of the present invention. In the course of an analysis procedure, multiple particles to be analyzed are associated with and contact one or more capture zones (step 100). The capture zones are designed to capture particles having certain surface properties. The contacting of the particle with the capture zone may be accomplished through gravitational settling or more actively applied forces, such as centrifugation, application of a magnetic field to magnetic particles, or the use of optical tweezers (including the use of HOT). If the particle density is too low for gravitational settling, the latter active methods may be preferable. An optical force is then applied to the particles in a manner that tends to perturb the position of the particles (step 110). The optical force may have a component that is normal to and oriented away from a capture zone (e.g., an out of plane force when a planar capture zone is used). The optical force may also have a component that is parallel to the surface or a plane of a capture zone. The optical force may also be designed to move the particles diagonally in a plane orthogonal to the plane of a capture zone (e.g., to attempt to accelerate the particle so as to displace it in both a horizontal and vertically direction). The magnitude and orientation of the force may be constant, moving according to a preset pattern, or moving in accordance with feedback obtained by observing the particle and may tend to perturb the particle in a variety of ways that are dependent on the binding-state of the particle with respect to the capture zone. In addition to movement in straight line the forces, or timed pattern of forces could induce the particles to spin, twist or otherwise deform (if flexible) move to and fro, or exhibit combinations of the aforementioned behaviors. A sensing module of an appropriate apparatus (e.g., the automated microscope of FIG. 8, described below) is used to determine the presence or degree of perturbation of the particles in response to the force (step 120). For example, the particle may be dislodged and displaced from the capture zone as a result of applying the optical force. The sensed response of the particle to the force is used to determine a property of the interaction between the particle surface and the capture zone. Properties that may be determined include the presence, absence or quantity of a chemical species on the surface of the particle or the capture zone. Alternately, the sensed response may be used to determine a characteristic of the environment in which a particle and capture zone interact (e.g., presence or amount of competitive binders, temperature, allosteric effectors, or solution properties).

In specific embodiments, a capture zone includes probes with a specific binding affinity for a particular chemical species. The relative or absolute tendency of a particle in contact with such a capture zone to resist displacement by an optical force indicates whether the chemical species for which the probes are specific is present on the surface of the particle. In embodiments, the quantity or concentration of the chemical species on the particle may also be determined. In other embodiments, including those described with reference to FIGS. 24-25, the interaction of a particle and capture zone is used to analyze the presence, absence or quantity of an analyte in solution. As described below, a specific illustrative embodiment of the method of FIG. 1 includes associating the particles with the capture zones by introducing a sample into a microfluidic cartridge and allowing cells present in the fluid sample to settle under the force of gravity to contact an antibody coated capture zone. The cartridge is then inserted into an automated device that locates the cells on the capture zones, applies a force, and senses positional changes of the cells in response to the force in order to make determinations about the surface antigens present on the cells and arrive at a blood type.

Because many important applications of embodiments of the present invention are biological or biochemical in nature, in examples described herein, the particles analyzed are cells. However, many other types of particles may be characterized including, without limitation, viruses, vesicles, organelles, silica microspheres, polystyrene or other polymeric microspheres, microspheres with sample analyte molecules attached, irregularly shaped microstructures, fluorescently or otherwise labeled microstructures, bar-coded microstructures (including nucleic-acid encoded identifiers, fluorescent or Raman-active identifiers, etc), and inorganic structures including semiconductor, core-shell nanoparticles, quantum dots, magnetic microspheres, and metal structures. Particles may be, for example, in the 0.1 to 100 micron size range, and in particular embodiments are between 1 and 10 microns in diameter. Generally, the particles should be optically active in the sense that they are susceptible to the optical forces at some wavelength used for analysis in a given medium.

Figure 2:
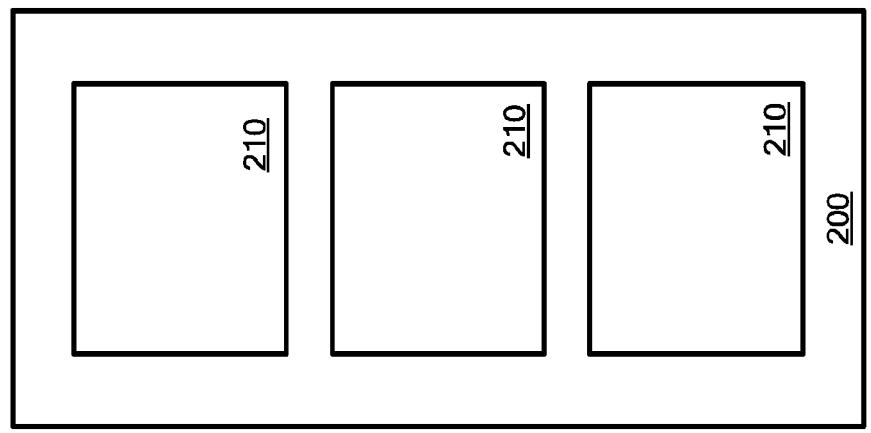
FIG. 2 is plan view of an apparatus having capture zones for use with the method of FIG. 1.

FIG. 2 shows a plan view of a substrate 200 with a plurality of capture zones 210. Each capture zone has a surface that is functionalized with probes for a particular chemical species. As for immunoassay and biochip binding surfaces, the capture zones 210 may have an ensemble of immobilized probes in capture zones. The substrate 200 may be transparent to various wavelengths of light to allow optical imaging of particles and application of optical forces via illumination from the side opposite the probes although in alternate embodiments illumination is from above, or via both paths. The probes may be covalently linked to the surface, for example, by using silane or other suitable chemistry on a glass substrate 200, and may employ epoxy, thiol, amine, or other reactive groups as is known in the art. One specific scheme for attaching antibody fragments is described below with reference to FIG. 21. The capture zones 210 may also include non-planar structures that are attached to the substrate, for example, gel-pads (see, e.g., the disclosure of U.S. Pat. No. 6,642,000), wells, capillaries, or other structures. Three capture zones 210 are shown, but more or less may be provided. The substrate 200 may be essentially immobile and incapable of being moved with the optical forces used to test the particles. Alternately the capture zones 210 may be manipulable in parallel with optical tweezers to form a three dimensional array (e.g., the capture zones 210 are disposed on the surface of optically active particles). U.S. patent application Ser. No. 10/173,539, filed Dec. 12, 2003, and incorporated herein by reference discloses the creation of three dimensional arrays.

As mentioned above, capture zones 210 include probes that have a specific affinity for a given chemical species. In other words, the capture zone selectively binds to one species with a higher affinity than to others that are likely to be present in an analyte sample. Accordingly, binding interactions of entities in a test sample with a capture zone are indicative of the presence in that sample of the chemical species for which the capture zone was designed to have a specific affinity. Examples of probes which can be used with the embodiments of the present invention include nucleotides, oligonucleotides (and chemical derivatives thereof), linear or circular DNA (e.g. plasmids, cosmids, BACs, ACs), messenger RNA, cDNA, mitochondrial RNA, artificial RNA, aptamers, PNA (peptide nucleic acids), polyclonal antibodies, monoclonal antibodies, recombinant, engineered antibodies, antibody fragments, antigens, haptens, antibody FAB subunits (modified if necessary), domain antibodies, artificial antibodies, proteins, modified proteins, recombinant proteins, recombinant antigens, enzymes, enzyme cofactors or inhibitors, protein complexes, lectins, Histidine labelled proteins, tagged proteins, molecular imprints, plastibodies, membrane receptors, whole cells, cell fragments and cellular substructures, synapses, agonists/antagonists, cells, cell organelles, (e.g., microsomes) small molecules (such as benzodiazepines, prostaglandins, antibiotics, drugs, metabolites, drug metabolites, natural products), carbohydrates and derivatives (including immunodominant sugars), steroids, hormones, peptides, native or artificial polymers, natural and artificial receptors and chemical derivatives thereof, chelating reagents, crown ether ligands, supramolecular assemblies, indicators (pH, potential, membrane potential, redox potential), and tissue samples (tissue micro arrays).

FIG. 3 shows a specific embodiment in which a planar substrate 200 that has capture zones 210, which are functionalized to include antibody probes for red blood cell surface antigens in accordance with an embodiment that is useful for blood-typing, including the determination of minor and rare blood types. A first capture zone 210 is functionalized with one or more species of antibodies that selectively bind to A antigens (anti-A antibodies), a second capture zone 211 is functionalized with one or more species of antibodies that selectively bind to B antigens (anti-B antibodies), a third capture zone 212 is functionalized with one or more species of antibodies is functionalized antibodies that selectively bind to Rh factors (anti-Rhesus factor antibodies). Additional capture zones may be provided as needed to test for additional antigens (e.g. to test minor or rare blood types involving 4, 5, or even 10 or more antigens.). In use, a small droplet of blood (e.g., 0.1-10 microliters) is taken from a patient using a lancet and is diluted with buffered isotonic salt solution that contains an anticoagulant (e.g., heparin, metal chelators (e.g., EDTA, citrate/ACDA) EDTA, Warfarin, or other clotting inhibitors). The diluted blood sample is dispensed to the substrate and cells within the blood sample are allowed to settle and thereby contact the capture zones on the surface. Settling will occur through a sedimentation process under the force of gravity, but centrifugation, magnetic separation or other method could also be used. When, as is discussed further below, the solution above the sample above the surface 200 is kept to a suitably low height, gravitational settling of a suitable number of particles will occur in a rapid manner (e.g. less than 10 minutes, 5 minutes or 1 minute), obviating the need for these other methods. The magnitude of the dilution is chosen to allow a plurality of red blood cells 220 to settle in each capture zone to allow for measurements to be made using multiple cells for each cell-surface antigen determination. As an example, a 1000 fold dilution of whole blood may be made using a diluent composed of buffered saline with an anticoagulant (e.g., phosphate buffered or Tris buffered saline with EDTA). Lymphocytes 230 may also settle on the capture zones 210 if the sample is diluted whole blood, but being in a minority, these cells may be ignored, although in alternate embodiments, the lymphocytes may be analyzed instead of or in addition to the RBCS. Although shown as separate zones, the captures zones 210 may also be continuous, as long as the boundaries of each zone are known (e.g., through observation of demarcation on the substrate or relative position to a reference surface). Optionally, the capture zones 210 may be separated by physical barriers including solid walls of chambers or wells, or through manipulation of surface energies of the substrate to create hydrophobic or lyophobic interstitial regions.

An software-based image recognition routine is used to identify a red blood cell 220. Identification of the red blood cell 220 may employ automated microscopy and image recognition to distinguish it from lymphocytes 230 or other objects. The image recognition routine may identify the red blood cells based on recognition of various features including, but not limited to: red color, high contrast, size, circularity, and continuity of edges. The image recognition routine may take into account the effects of image focus and may utilize images with no objects in the field to subtract background. The health of the cell may be also be analyzed; contrast is one indication of cell-health. Based on this analysis of cell-type and health, one or more cells 220 are selected and an optical force is applied to the cell or cells 220. The optical force may be in the form of an optical tweezer or optical trap, and in embodiments, is applied using holographic optical tweezers. The force has a component that is oriented away from the surface 200 so that the force, if sufficient in magnitude, will tend to displace the cell 220 from the surface (and optionally further in the same or another direction). Typically, the potentially displacing force component is in a direction that is orthogonal to the plane of the substrate 200, but could also be in or near the plane of the substrate to generate sideways displacement. If the force is sufficiently strong to displace a cell 220 that does not contain the antigen recognized by the antibody of a given capture zone 210, but insufficiently strong to dislodge a cell 220 that does contain the recognized antigen, then displacement of the cell 220 will indicate the absence of that antigen on the surface of the cell 220 and lack of displacement will indicate the presence of the cell-surface antigen on the cell 220. This process may be repeated from multiple cells within each capture zone 210 to arrive at statistically significant results. This process may also be performed in parallel so that forces are applied to multiple cells 220 concurrently and the displacement of the cells 220 is also sensed in parallel. In a specific embodiment, parallel processing is accomplished using HOT.

Thus, many benefits accrue by using methods and devices described herein. Using multiple probes types in a parallel or serial manner allows for a more complete characterization on amenable particles, e.g. analysis of RBCs to determine a blood type or sub-type. This process may be performed in a rapid manner, e.g., under 5 to 10 minutes, especially by employing parallel processing and settling of particles from a low height liquid layer. As described below, including with respect to FIGS. 22a-25, the aforementioned techniques may be applied to a variety of assay types.

As mentioned above, the optical force may be in the form of an optical trap, which may be described by a force-field having a center and radiating sloped regions, so that a particle positioned in the sloped regions will have an elevated potential energy and, absent a resisting force, tend to be displaced toward the center. An optical trap may be centered on a cell 220 and the trap moved away from its initial position relative to the substrate 200 to test the affinity of the cell 220 for a capture zone 210. In this mode, a dislodged cell will tend to move with the center of the trap. Alternately, the trap may be centered at a distance from a cell 220, but close enough to still exert an optical force on the cell 220. In this configuration, a weakly bound cell will tend to accelerate toward the center of the trap and remain there. The optical trap may also be placed at a distance from the cell 220 in both a vertical and horizontal direction so that the force will tend to displace the cell 220 in a diagonal manner. In either configuration, the dislodging optical force may be applied at a constant level to give a qualitative result, or gradually increased over time to quantify the affinity of the cell 220 for the capture zone 210. In this quantitative embodiment, the dislodgment force (a parameter related to the applied optical force at which the cell 220 is dislodged from the capture zone 210) may be compared to known, or contemporaneously measured reference values. For example, "standard" particles that are coated with antigen may be included with the diluent and the dislodgment force of the cells 220 may be compared to the dislodgment force for the particles. These particles may be designed to be stable when stored for long periods of time (e.g., constructed from glass particles coated with antigens, antigen—mimics, or in other embodiments, probes). The dislodgment force for a cell 220 or other particle in a given capture zone 210 may also be compared to the dislodgment force for a control or reference capture zone 210. For analytical purposes, there may be no need to apply a force large enough to dislodge specifically bound particles that are recognized by the capture zones if sufficient force is applied to displace unbound or non-specifically bound particles. However, in some cases, it may be desirable to "rip" such cells or other particles from the capture zone for further analysis or use (e.g., to grow in a cell culture, analysis of nucleic acids or proteins in the cell, etc).

If a capture zone 210 has a very low avidity for a given particle and the particle is displaced by the application of an optical force, the most that can be determined is that the binding force between the particle and the capture zone 210 is less than the displacing force. Likewise, if a capture zones 210 has a very high avidity for a given particle and the particle is not displaced by application of an optical force, the most that can be determined is that the binding force between the particle and the capture zone 210 is greater than the displacing force. Thus, if desired, the surface properties of cells 220 or other particles may be quantitatively determined over an increased dynamic range by testing the affinity of the particles toward capture zones 210 having varying avidity for the particles.

Figure 4:
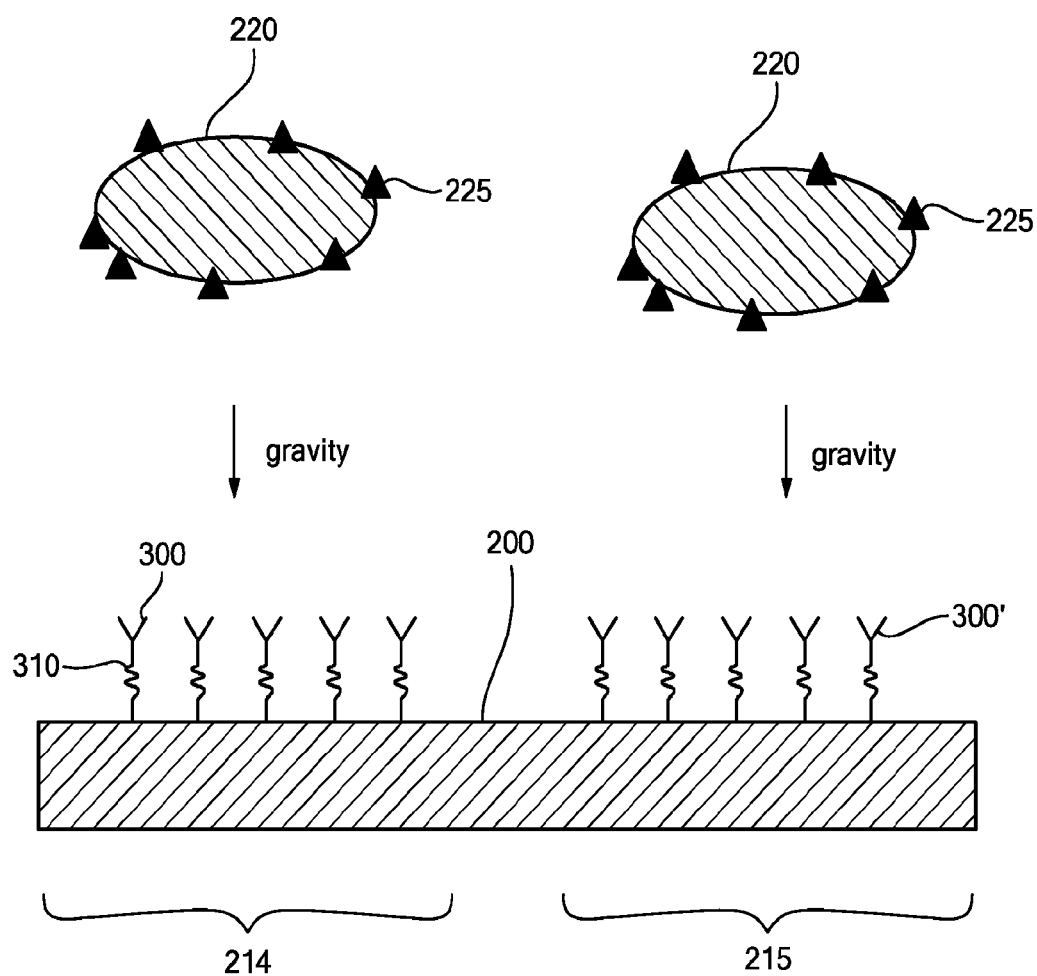
FIG. 4 is a schematic diagram showing a cross sectional view of the apparatus of FIGS. 2-3 including capture zones with antibody probes.

FIG. 4 shows a schematic cross sectional view of a substrate 200 having two capture zones 210 (designated 214 and 215), each having a selective binding affinity for a different blood group antigen 225 of a red blood cell ("RBC") 220. Antibodies 300 raised to a first antigen are attached to the substrate 200 at capture zone 214 via a linker 310. Antibodies 300' raised to a second antigen (different from the first antigen) are attached to the substrate 200 at capture zone 215 via a linker 310. Much is known in the art regarding methods for attaching antibodies to glass, plastic or metal surfaces. For example, a variety of silane coupling chemistries and homo-functional or heterofunctional cross-linkers are available from Pierce Biotechnologies (Rockford, Ill.) and from Gelest (Morrisville, Pa.). However, as explained more fully below, probe immobilization methods and structures that are optimal for use with methods of the present invention may present a new set of challenges.

Figure 5:
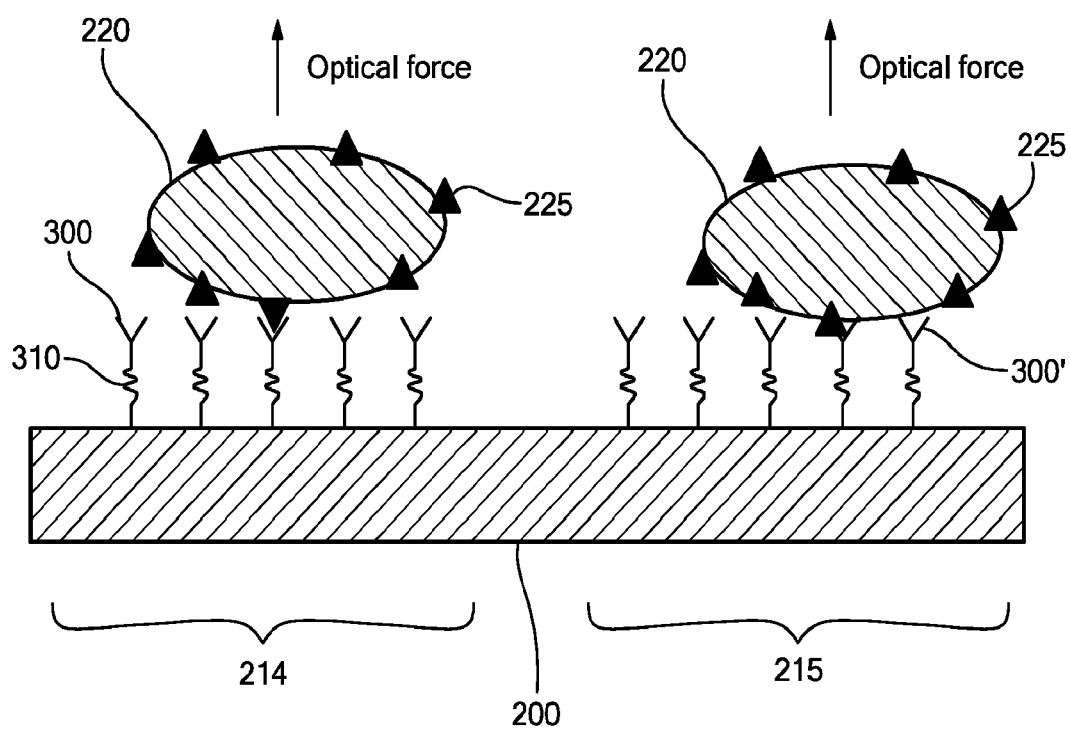
FIG. 5 is a schematic diagram showing the apparatus of FIG. 4 after cells have settled on the capture zones.

FIG. 5 shows the red blood cells 220 after they have settled under the force of gravity, with the result that they are now in contact with the antibodies on the surface of the substrate 200. Although some non-specific binding may occur between antibodies 300, linkers 310, or the surface of the substrate 200, the presence of cell surface antigens 225 on the cells 220 for which the antibodies 300 in a given capture zone are specific will cause these cells 220 to adhere more strongly to the substrate 200 so that when an appropriately sized and oriented optical force is applied, those cells 220 that have the recognized antigen 225 will remain and those cells 220 that do not have the recognized antigen 225 will be displaced in a direction away from the capture zone (item 214 or 215).

The strength of binding of a cell 220 will be determined by several factors including the affinity of the antibodies 300, 300' for the antigens 225, the areal density of antibodies 300, 300' on the substrate 200, and the density of the antigens on the surface of the cells 220 (although many cell surface antigens are able to "float" in the cell membrane and concentrate in one region). The overall binding force resulting from multiple probe-target interactions (here, antibody-antigen interactions) is termed the "avidity" of a capture zone.

If the red blood cells 220 are added in a thin liquid layer (e.g. 1 mm to 0.5 mm or less, or even as thin as the approximate height occupied by one to two monolayers of red blood cells), the red blood cells will contact the captures zones 214-215 rapidly (e.g. less than 10 minutes). Some additional incubation time may be needed to allow optimal binding interactions between the cells 220 and captures zones 214-215, due to translocation of cell antigens, morphological changes in the cell, or other effects. Nonetheless, the overall time for the biding reaction to reach a point that is sufficiently close to equilibrium is very short compared to traditional immunoassay techniques, which may require many hours of incubation to allow for binding through combinations of convection and diffusion.

Particle surface analysis methods described herein may utilize a dedicated instrument with a limited ranges of optical force strengths. Limiting the optical force strength to a range may be advantageous because use of too much optical energy (e.g., because cells are too strongly bound) may damage to cells or antibodies, increase the local temperature (which may cause fluid flow), or otherwise degrade the resulting measurements. Conversely, use of too little optical force (in conjunction with weakly bound cells) may result in a poor dynamic range and low confidence in the experimental data. Accordingly, an embodiment of the present invention employs a substrate with captures zones 214, 215 that are tuned to possess an avidity for the cells 220 that is within a specified range. For example, the range may be 1 to 1000 pN. However, to avoid undue optical heating effects while maintaining sufficient signal/noise, the range may be chosen to 10 to 200 pN, or 20 to 100 pN. In an embodiment, the avidity is tuned for use of optical forces of the magnitude produced by HOT with illumination at 1064 nm and having a power of about 500 mW per trap.

Figure 6:
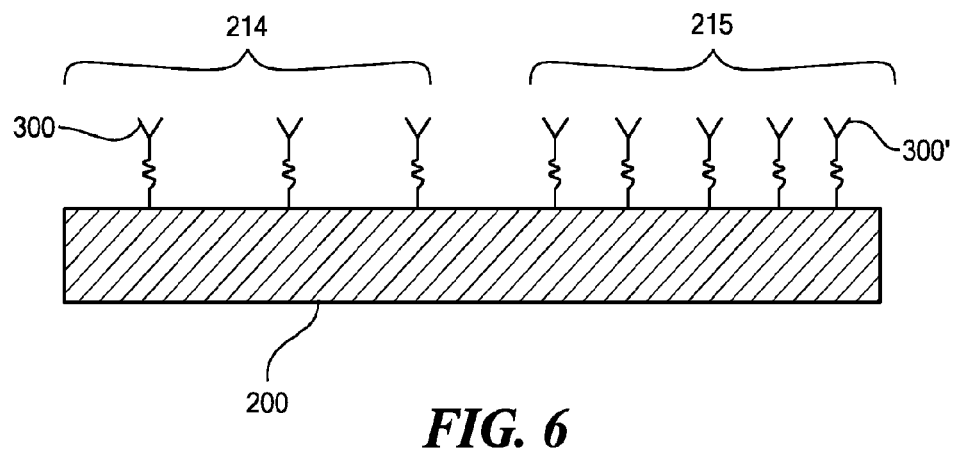
FIG. 6 is a schematic diagram showing the apparatus of FIGS. 2-4 in cross section and illustrating varying probe densities.
Figure 7:
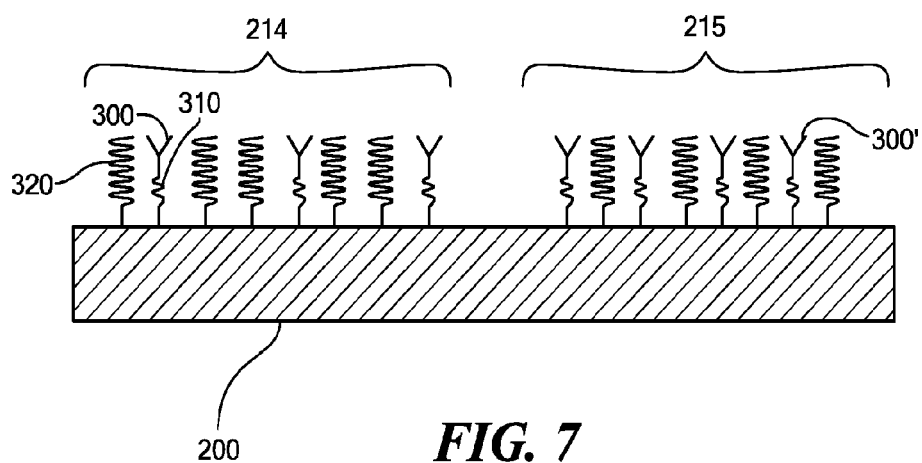
FIG. 7 is a schematic diagram showing the apparatus of FIGS. 2-4 in cross section and illustrating the use of bioinert moieties.

FIGS. 6 and 7 schematically illustrate substrates 200 with tuned capture zones 214 and 215. In FIG. 6, the areal density of the antibodies 300 is adjusted: capture zone 214 has a lower density and capture zone 215 has a higher density. Manufacture of such capture zones may be accomplished be limiting the amount of silane, crosslinker, or antibody and may involve the use of reactive and non-reactive blocking agents. Avidity may also be altered by varying crosslinker length (e.g. from 5 to 50 carbon atoms).

FIG. 7 shows capture zones 214 and 215 that include both antibodies 300 and bioinert moieties 320. The bioinert moieties 320 may be, for example, hydrophilic polymers such as polyethylene glycol moieties linked to the substrate 200 via a silane linkage. The bioinert moieties 320 serve to reduce the antibody density with a minimal or negative contribution to nonspecific binding interactions between the cells 220 and the capture regions. Bioinert moieties may also be included on regions between capture zone, if present. The linker 310 may also be bioinert or have a bioinert component. The areal density of antibodies 310 may also be altered by combining the antibodies with a reactive but bioinert reagent; e.g., glycine when amine-reactive crosslinkers are used or cysteine when sulfhydryl reactive crosslinkers are used.

Flexible particles, like cells 220 may also deform to become flat when bound strongly to a capture zone 214, 215. As a result, it may be difficult to recover a cell using optical force. Although recovery of the cells is not necessary for simple analytical methods such as blood typing, in other applications a user may desire to recover the cells for further experimentation or use. If rigid particles such as glass microspheres are to be analyzed, the geometric mismatch between a flat substrate 200 and a curved particle will limit the effective avidity of the interaction between the particle and the capture zone. Accordingly, by choosing flexible linkers 310 having a length that is significant on the scale of particle curvature, a cell 220 or other particle may be bound to a capture zone 214 while retaining a greater degree of curvature. For example, the length of the probes may be adjusted to be greater than 10 nm, 100 nm, or 1 μm. Alternately, a substrate 200 having regions of curvature on the scale of the particles (e.g., microwells or capillaries) may be used to better complement particles positioned therein. In this alternate embodiment, optical tweezers may be used to position the particles in the curved regions.

Figure 8:
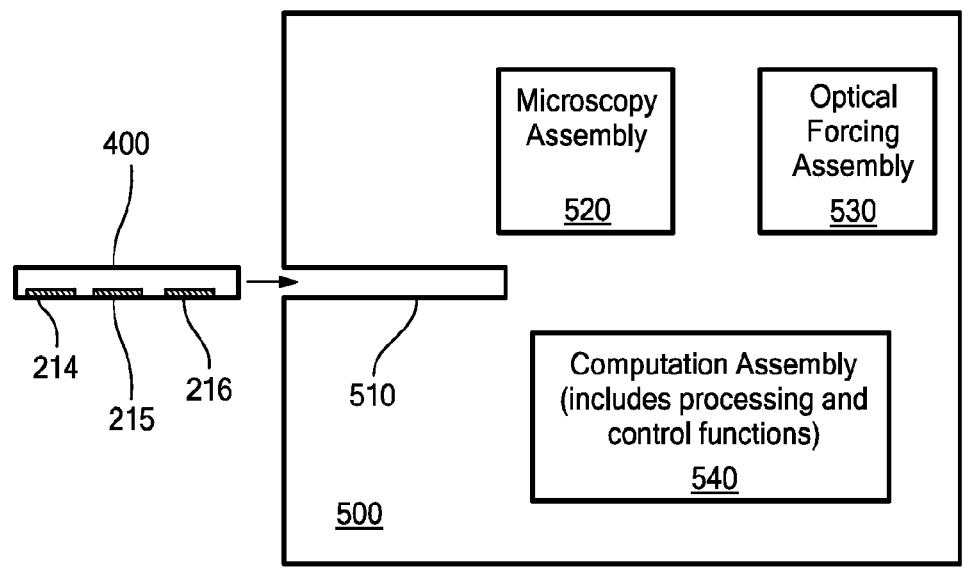
FIG. 8 is a schematic diagram showing a system that includes an analytical cartridge and an instrument in accordance with an embodiment of the invention.

FIG. 8 is a schematic diagram of a highly automated system for performing the method of FIG. 1 in accordance with an embodiment of the invention. A fluidic cartridge 400 has multiple capture zones 214, 215 and 216. In use, the cartridge 400 is filled with a sample to be analyzed and mounted in an optical instrument 500 by positioning the cartridge 400 in a jig 510 of the instrument 500. The cartridge 400 can be loaded and unloaded in the jig 510 manually or, for more fully automated operation, manipulated robotically. In an embodiment, the jig is accessed by lifting a hinged lid of the instrument 500. The instrument includes a microscopy assembly 520 and an optical forcing assembly 530. The microscope assembly includes optics for locating particles associated with the capture zones 214-216 and for sensing the response of the particles to application of an optical force by the optical forcing assembly 530. The optical forcing assembly 230 uses information related to the position of the particles on the capture zones 214-216 and applies forces to the particles which are of an orientation and magnitude as to tend to displace weakly bound or unbound particles yet sized to not dislodge strongly bound particles that are recognized by probes of the capture zones 214-216 that are specific for chemical entities on the surfaces of the particles. Alternately, the optical forcing assembly 530 applies a varying force, the microscopy assembly senses the responses of the particles to those forces and a computation assembly 540 records the force level applied at the time of particle displacement. In an embodiment, the optical forces are generated via optical holographic tweezers (HOT). The use of HOT has the advantage of allowing a common focal plane for the imaging and forcing optics (since the HOT trapping plane can be optimally adjusted to work with a specific microscopy assembly) and also allows for application of force to multiple particles concurrently, even if the particles are disposed at a plurality of sites in three dimensions. The micropy assembly 520 and optical forcing assembly are controlled by the common computation assembly 540. The computation assembly 540 may include a processor, control circuitry, a data storage medium, and data input/output subassemblies, and may include a personal computer, or dedicated application specific hardware. Components of the computation assembly 540 may be physically separated and even may reside outside of the instrument 500 (e.g., on a computer network), but will be in data communication in order to execute the methods described herein. Unlike prior art systems, the instrument 500 may be capable of optically forcing and sensing the displacement of multiple particles simultaneously. The computation assembly 540 may perform analysis and presentation of the data to a user and may associate assay results with machine readable identifiers (e.g. bar codes, RFID tags and the like) that are directly or indirectly (e.g. packaged with) associated with fluidic cartridges 400.

The fluidic cartridge 400 may be configured to make use of a very small sample size of the biological component being examined. Using only a few cells of the biological component in question greatly reduces the amount of sample needed, which expedites the diagnostic tests for the laboratory. Due to the reduced sample size, each sample collected may be used to perform more diagnostic tests. Also, reducing sample sizes reduces pain and discomfort of the donor of the sample.

As shown in the embodiments of FIGS. 9-13, the fluidic cartridge 400 may be configured with internal reservoirs, capillaries and passageways that promote the introduction of liquid samples and movement of the samples. Optionally, the fluidic cartridge will facilitate mixing with diluent or other substances using a variety of conventional or microfluidic principles, as are known to one of skill in the art. In the simple, and low cost configuration shown, the fluidic cartridge 400 makes use of the scientific principle of surface tension in order to achieve passive flow through the cavities in the fluidic cartridge 400. Capillary action, fluid flow direction and velocity are regulated by varying surface wetting properties and the geometric size of the internal channels and cavities. The fluidic cartridge 400 may also rely on fluid flow created by other forces such as gravitational, pneumatic, hydraulic, mechanical or electro-osmotic actuating forces, including light-actuated mechanisms.

In an embodiment, the fluidic cartridge 400 is configured to have an inlet port into which a user may introduce a small quantity of sample fluid. The fluid sample, such as blood, if practicing a blood-typing diagnostic test, is directed to a sample reservoir by capillary action. The sample fluid is introduced to an interrogation chamber wherein the sample may be assayed. In the context of a blood-typing procedure, the interrogation chambers (also referred to herein as "sample chambers") may include capture zones. After the sample interacts with the capture zones, HOT may be used to assay the resulting interactions of the sample. Additionally, the fluidic cartridge 400 may be configured to have one or more outlet points that allow for the escape of gases or allow the user to further control in sequence the fluid flows through the holder.

Figure 9:
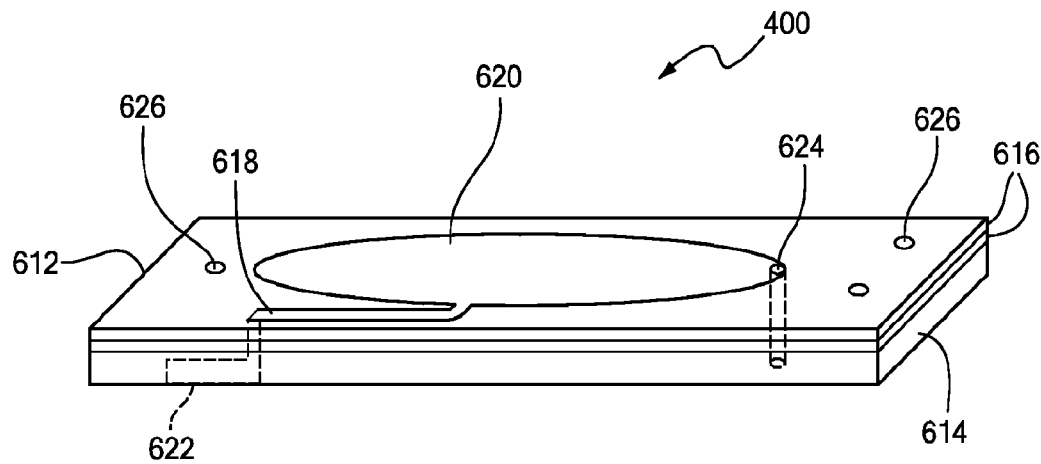
FIG. 9 is a schematic diagram showing, in perspective view, a cartridge in according to an embodiment of the invention.
Figure 10:
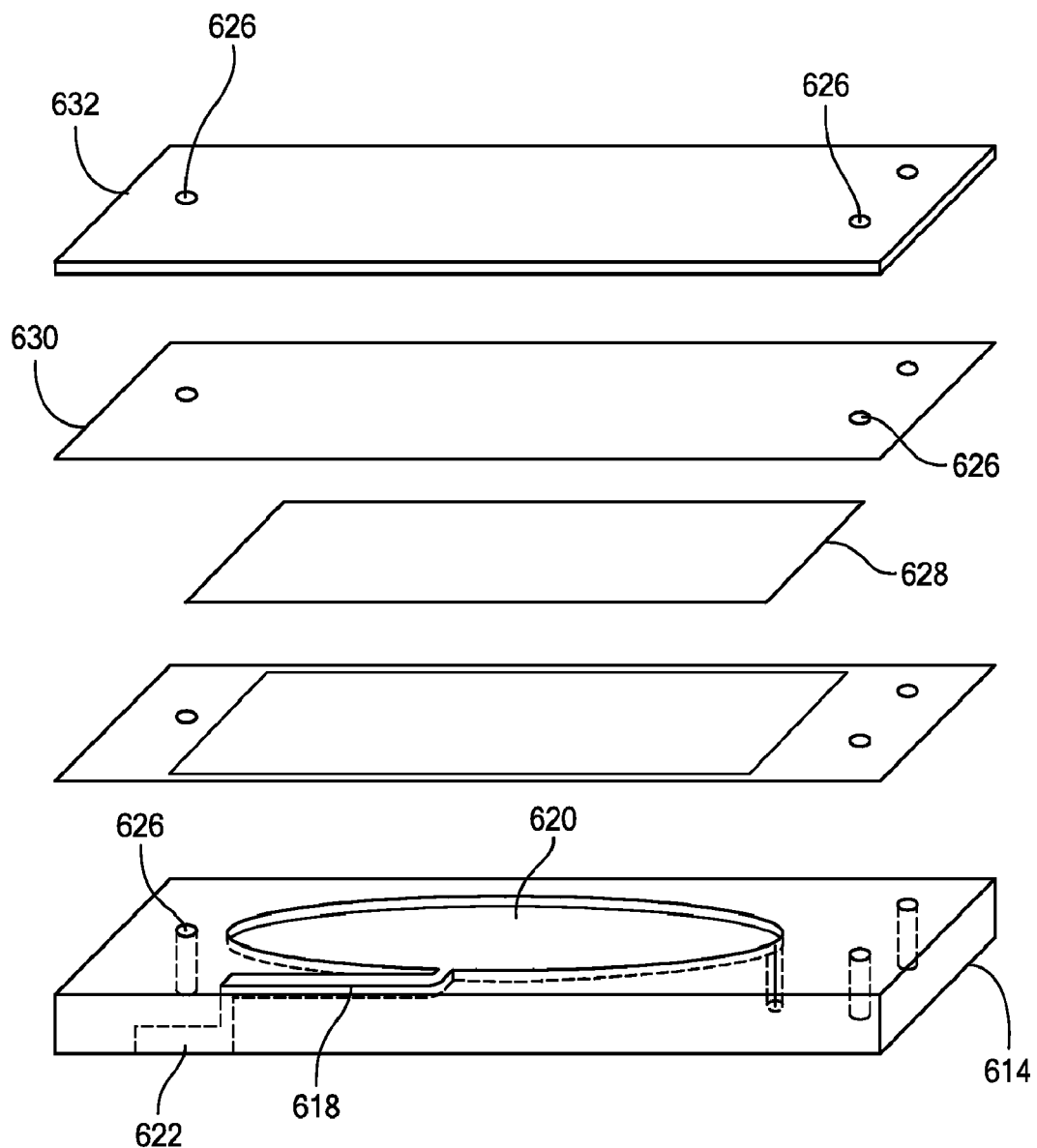
FIG. 10 is an exploded view of the cartridge of FIG. 9 manufactured by laminate assembly in accordance with an embodiment of the invention.
Figure 11:
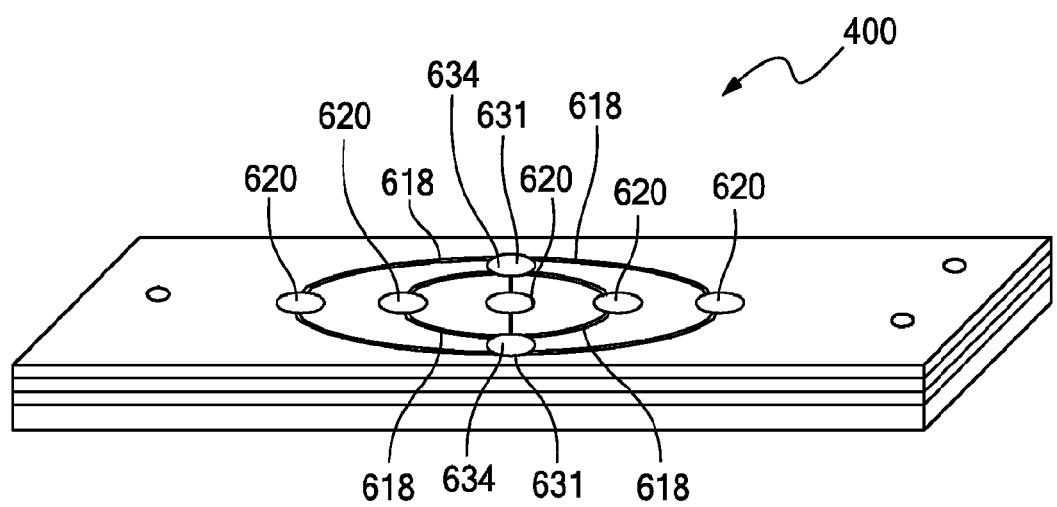
FIG. 11 is a cartridge having multiple analysis chambers in accordance with an embodiment of the invention.

FIGS. 9-11 show an embodiment of the fluidic cartridge 400. The fluidic cartridge 400 may be formed from a plurality of polymeric laminate substrates. Various configurations of internal configurations and shapes can be formed in multiple layers of plastic sheets by cutting techniques such as laser ablation. Alternately, components may be made by conventional machining, injection molding, 3D printing, photo-etching or other techniques. The resulting sheets and a cover slip are bonded using adhesive, ultrasonic welding or other technique to form a laminate substrate with a shaped internal cavity. The laser cutting can create points, channels, valves, reservoirs, and other fluidic features in the fluidic cartridge 400.

FIG. 9 is an illustration of a fluidic cartridge 400 according to an embodiment of the present invention. The fluidic cartridge 400 includes a body 612 that may be formed from a plurality of polymer layers. A base 614 is formed from a plurality of layers of polymer with adhesive layers sandwiched between them. Cavities in the base 614 form at least one capillary 618 and one or more analysis chambers 620 when covering layers 616 are added during manufacture of the cartridge 400. Also formed in the fluidic cartridge 400 is at least one inlet port 622 for introduction of the sample. An outlet port 24 may also be provided for allowing gas to escape, for withdrawal of a sample or for controlling flow in the holder when a syringe is applied through the port. Alignment holes 626 facilitate alignment by placement over corresponding alignment pins on a fixture (e.g., item 510 of FIG. 8) and may be used for aligning the various layers during assembly and bonding. In FIG. 9, the inlet port 622 (and outlet port) is cut into the base 612 of the cartridge 400 while the capillaries 618 and analysis chamber 620 are cut into the top surface of the base. When the top layers are added to seal the capillaries 618 and chamber 620, the cartridge 400 can be turned over with the inlet port left open. The inlet port, and every port of the fluidic cartridge 400, can be sealed with a membrane that keeps interior passages sterile and permits introduction of sample (and withdrawal) only by hypodermic needle.

FIG. 10 shows an exploded view of the cartridge 400 of FIG. 9. The fluidic cartridge 400 may be fabricated and assembled using techniques based on laser ablation of polymeric laminate. Multiple layers of plastic sheets are laser cut and bonded to form a laminate chip which includes ports, channels, valves, reservoirs and other fluidic components. The layouts of the multilayer laminate chip are first prepared using CAD software, such as AutoCAD. Each layer is then cut using the Universal Laser Systems $CO_2$ laser cutting system by conversion from the CAD file. The base 614 layers are then bonded together using thin layers of optically clear pressure sensitive adhesive to form three-dimensional structures. A variety of plastic materials, including polyester, acrylic and silicone elastomer, may be used as base layers. Each base plastic layer is sandwiched by two layers of pressure sensitive adhesive protected by siliconized release backing layers. After laser cutting, the release layers are removed, and the cut parts are aligned on a set of posts fit though alignment holes 626 cut into each layer. Layers are stacked to create thickness. After pressing them together, the assembled structure can be pressed through rollers of the laminating machine. This process can be repeated to form multiple layer structures. After the base 614 is created with the desired shapes for capillaries and chambers, covering layers 616 are added. In particular, a cover slip 628, just large enough to cover the cut-out chambers and capillaries, but not the whole substrate, is applied. The cover slip 628 is surrounded by an adhesive layer 630 (applied to the base but with a window for the cover slip to pass through). Another adhesive layer is applied over the top of the cover slip and a transparent polymer cover layer is applied over the adhesive and cover slip to close the base 614 and create the enclosed fluidic cartridge 400 The complete fluidic cartridge 400 may be of a standard size that can be held on a standard microscope stage; e.g., approximately 1 inch by 3 inches. The materials used for the fluidic cartridge 400 that bound the analysis chamber 620 should be transparent to light so that the fluidic cartridge 400 can be illuminated by microscope illumination and so that HOT laser energy can interact with the sample. The analysis chamber 620 includes one or more capture zones (e.g., item 210 of FIG. 2-3).

FIG. 11 shows a fluidic cartridge 400 with multiple sample analysis chambers 620 and connecting capillaries 618. The cartridge 400 has inlet ports 631 to allow user to introduce a small quantity of particle containing sample into the reservoirs 634 by capillary action. The sample then enters into capillaries 635 and analysis chambers 620 which allow particle sedimentation (i.e., settling) and interaction with capture zones. The sample may by introduced under pressure or, more conveniently, introduced using the capillary action of appropriately sized capillaries 618. In the above examples, the bottom surface of the cover slip 628 may have one or more capture zones functionalized for binding to a specific antigen that is hypothesized to be in the sample. After contact with the sample, the capture zones are probed with the HOT system and sample particles that have adhered to the capture zones may be "pulled" to check binding force. Comparing the experienced binding force with an established matrix of anticipated binding forces can confirm whether the specific chemical entity such as a cell surface antigen is present. In areas of where applications of the functionalized capture zones are used, it may helpful to coat the cover slip with other substances to help prevent occurrences of non-specific binding. Silane is a material that may be useful for this purpose as is disclosed in U.S. Pat. No. 5,620,857, the entirety of which is incorporated by reference herein.

Figure 12:
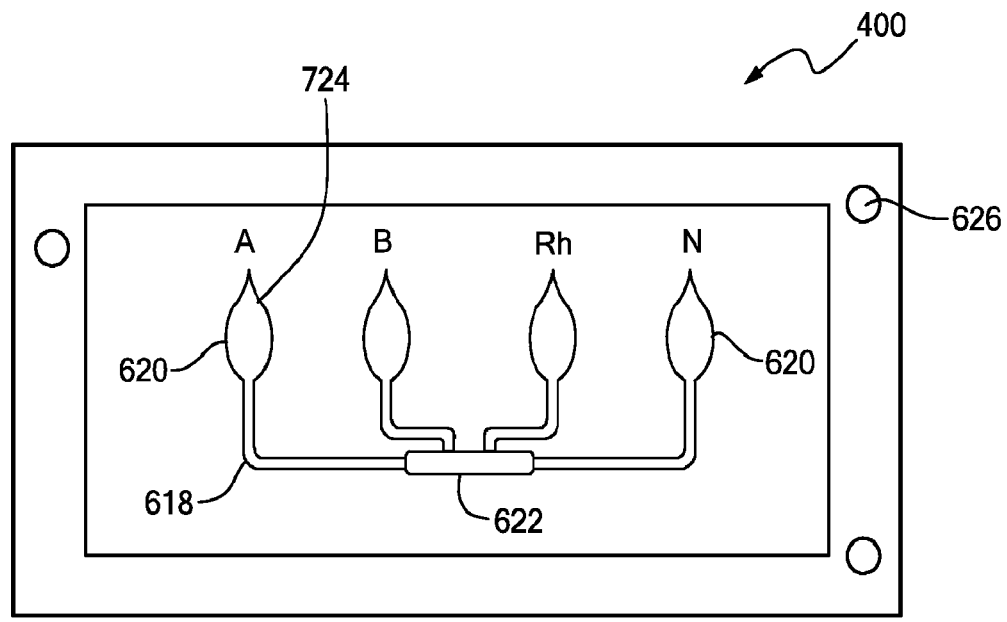
FIG. 12 is a cartridge having multiple analysis chambers in accordance with another embodiment of the invention.
Figure 13A:
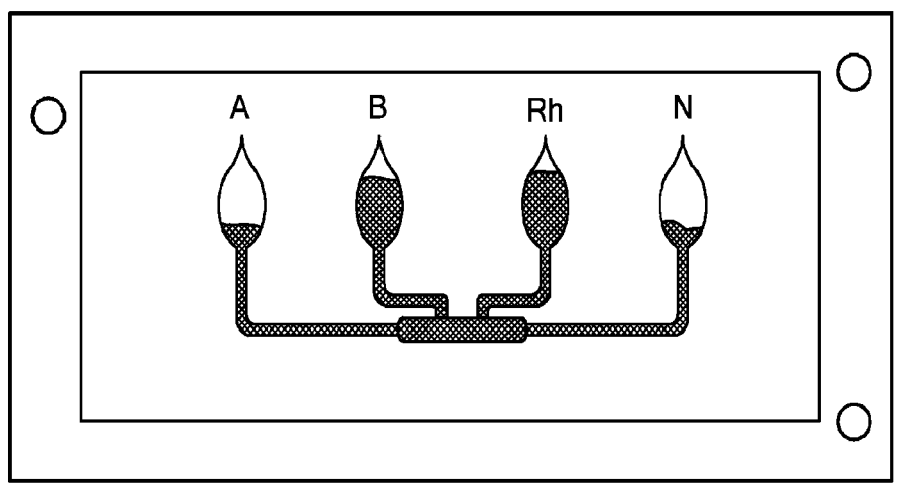
FIG. 13a shows the cartridge of FIG. 12 during the process of loading fluid into the cartridge by capillary action in accordance with an embodiment of the invention.

FIGS. 12 and 13a show an alternative configuration of a fluidic cartridge in accordance with an embodiment of the present invention. FIG. 12 shows a plan view of a sample cartridge 400 that is useful in performing particle analysis, including blood-typing according to embodiments of the present invention. The cartridge 400 includes a base 712. Alignment holes 626 allow for positioning within a jig of an analysis instrument 500. An inlet port 622 accepts a sample for analysis. When sample is applied to the inlet port 622, the cartridge 400 will draw the sample though multiple capillaries 628 and into sample analysis chambers 620, which may be isolated from each other. FIG. 13 shows the cartridge 400 in a partially filled state. Concurrently, trapped air will escape through exit ports 724. Eventually, the sample chambers will be completely filled with sample. Alternately, sample may be drawn through the cartridge by pumping or applying negative pressure via the exit ports 724. As described above, once the analysis chambers 620 are filled, particles will settle to contact the capture zones. The upper and/or lower surfaces of the analysis chambers 620 are optically transparent to allow imaging and optical tweezing so that particles may be imaged and subjected to optical forces to test for potential binding interactions with probes of the capture zone. Although shown in FIGS. 12-13 as having capture zones 210 for analysis of major blood group antigens, the cartridge 400 may be adapted for analysis of a wide variety of particle surfaces.

Because the sample chambers 620 of the cartridge 400 are separated from each other, the capture zones may be easily functionalized with different probes. For example, capture zones may be rendered reactive using a crosslinker molecule and different antibodies solutions may be simultaneously dispensed into the several chambers 620. Alternately, individual substrates (not shown) that are functionalized to create capture zones 210 may be placed and mounted in the several chambers 620. For example, the captures zones 210 maybe printed on glass chips, which are then mounted. Alternatively, multiple capture zones 210 are manufactured on a single continuous substrate (e.g., within chamber 620 of FIG. 9). The cartridge 400 may be constructed using the lamination method of FIG. 10. Alternately, the capillaries, chamber and inlet port may be machined or etched out of a block of base material, or a material may be molded with these cavities. An appropriate gasket and cover may then be affixed to the base. The cover may include a through-hole for sample access to the inlet port 622.

Figure 13B:
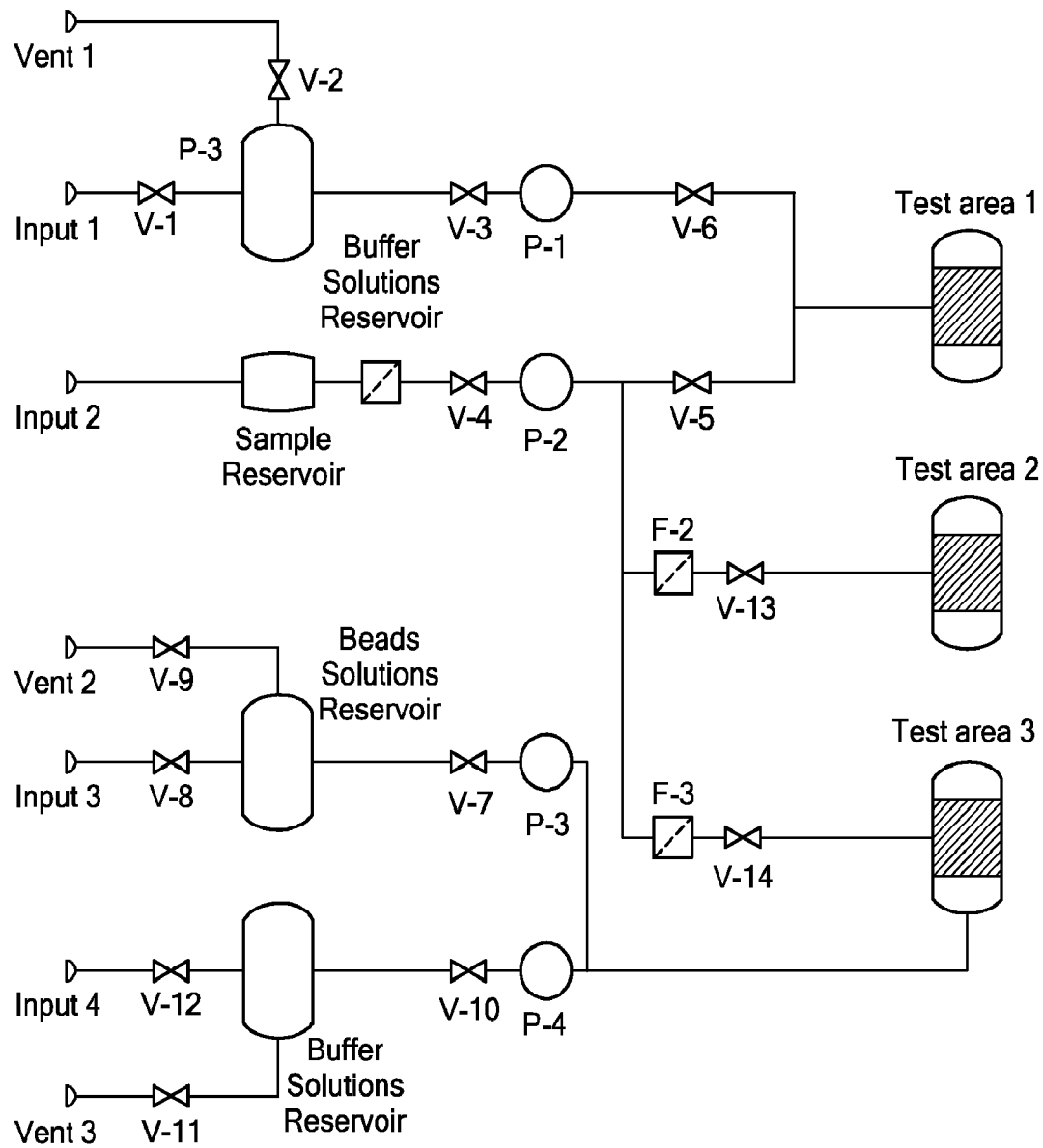
FIG. 13b shows an integrated fluidic sample cartridge in accordance with an embodiment of the invention.

FIG. 13b shows a schematic diagram of a highly integrated programmable fluidic cartridge 400 in accordance with an embodiment of the invention. The cartridge 400 is capable of automatically diluting a sample prior to analysis and automatically delivering reagents. The fluidic cartridge 400 includes built-in control valves and pumps, and inline filters, which can be remotely controlled and actuated, e.g., through pneumatic or electromechanical passageways. Optionally, the cartridge 400 can have internal sensors or pressure gauges to generate data for use in a feedback control loop. A variety of valves and pumps (e.g., flexible membrane valves and diaphragm pumps) may be included in the cartridge 400 for onboard fluidic manipulation and control. Before use in an analysis procedure, the cartridge has its buffer solution reservoir and beads solution reservoir preloaded. By keeping both the input valve and vent valve open, the buffer or bead solution is directed to its reservoir through capillary action. After the reservoir is loaded, the input valve and vent valve are closed. The cartridge now can be stored in a controlled environment for a long time before using it (e.g., manufactured and shipped to a user in a pre-loaded state). During use, the sample fluid, (e.g., whole blood in a blood typing procedure), is first introduced to the sample reservoir through the input port (input 2). By appropriate actuation of valve V3 through V6 and pump P1, P2, the blood sample can be mixed and diluted with buffer solution before entering into the test chamber (test area 1). A filter (PI) can help to remove contaminants or aggregates in the blood sample. A processed sample, such as a diluted blood sample, can also be filtered (F2 and F3) to remove unwanted material (e.g., cell or certain antibodies) before entering the test area. It is also possible to introduce (by controlling P3, P4 and Valve 7 through 14) particles or beads with specific surface properties to interact with processed samples and surface capture zones in the test area.

Figure 13C:
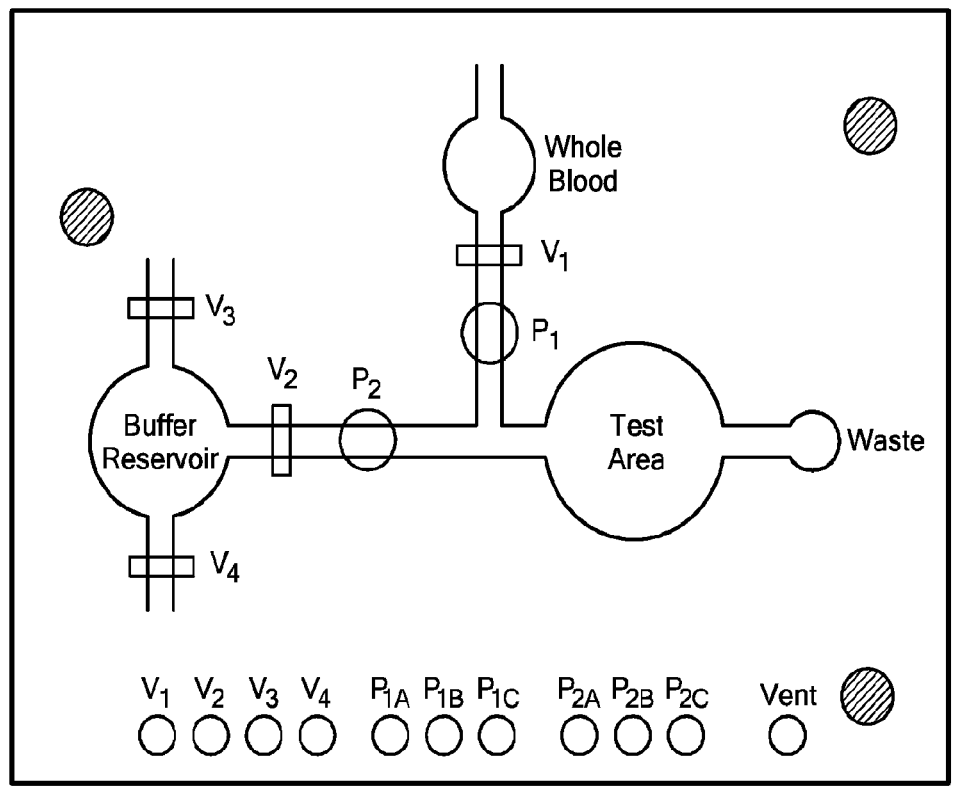
FIG. 13c shows another fluidic sample cartridge in accordance with an embodiment of the invention.

FIG. 13c illustrates another fluidic cartridge in accordance with an embodiment of the present invention. The cartridge can be formed from multi-layer polymeric substrates. The cartridge comprises a fluidic layer, which includes a test area, a buffer reservoir, a whole blood reservoir and all fluidic passageways, and a pneumatic control layer, which includes all pneumatic channels (not shown) that are distributed and used to actuate individual valves and pumps. The cartridge has connection ports (shown near the bottom of the cartridge) connecting those pneumatic control channels with external pneumatic or mechanical sources via integrated manifold. The valves are normally closed and can seal against normal fluid pressure inside the cartridge. Buffer solution is first introduced into the reservoir through capillary action or pressure driven procedure. The reservoir is then sealed by closing valves v3 and v4. After the blood is directed into the blood reservoir, the valve V1 and V2 are opened. By precisely controlling the pumping rate and volume, the buffer solution and blood sample are mixed and reliably primed into the test area.

In the embodiments of FIGS. 9-13c, the distance between the floor and ceiling of the sample analysis chambers may be selected to optimize the balance between the time needed for particles to settle, the achievable focal depth of the optical instrument 500, and the tendency of very narrow chambers to clog. For example, the cover of the chamber may be spaced apart from the base of the chamber by between 15 and 100 microns, to allow cells or other particles to settle to the capture zones within 10 minutes when vertically oriented with respect to gravity and held at room temperature. In another aspect, the cover and base may be spaced apart by between 2 to 10 times a diameter of a particle to be analyzed or between 3 to 5 times a diameter of a particle to be analyzed. In embodiments, the spacing may be adjusted so that the height of fluid held allows a substantial fraction, a majority or substantially all of any red blood cells in a solution to settle in less than 10 minutes. Noting that particles of differing size and density will settle at different rates, the chamber height may be adjusted accordingly.

FIGS. 14-19 show a compact HOT applications microscope instrument 500 that contains several complex systems that are interconnected within a portable package. In addition to containing all the components necessary for operating the HOT optical force application assembly and imaging functions, the device also includes user interface components. For example, the system may additionally include a monitor, keyboard, mouse and possibly a touch screen user interface display.

Holographic optical trapping, as the term is used herein, encompasses the use of holographic methods to generate optical gradient forces within a specified volume of a fluid, to allow for the manipulation of particles. Typically, monochromatic light (e.g., continuous wave laser light) is dispersed by a dynamic phase patterning optical element, namely a spatial light modulator (SLM) operated in reflection, such that the phase (and only the phase) of the reflected beam may be modulated in real time as a function of position within the beam. The nature of optical gradient forces is a well understood principle and can be implemented in the context of the invention by the use the terminology: HOT, optical tweezer, optical trap, optical vortices, optical bottles, optical gradient and more generally optical defined potential. Methods of holographic optical trapping are described, for example, in U.S. Pat. No. 6,055,106 ("Grier") filed Feb. 2, 1998 and U.S. patent application Ser. No. 10/1735,395 ("Gruber"), filed Dec. 12, 2003, which is incorporated herein by reference.

A substantially monochromatic optical beam is employed for generating a potential defined over a volume of fluid as provided by any suitable laser. Useful lasers include solid state laser; diode pumped lasers, semiconductor lasers, fiber lasers, fiber-hosted lasers, gas lasers, dye lasers, alexandrite lasers, free electron lasers, VCSEL lasers, diode lasers, Ti-Sapphire lasers, doped YAG lasers, doped YLF laser, diode pumped YAG lasers; and flash lamp-pumped YAG lasers. Diode pumped Nd:YAG lasers operating between 10 mW and 20 W are preferred. The preferred wavelengths of the laser beam used to form an optical force field for investigating biological material include the infrared, near infrared, visible red, green, and visible blue wavelengths, with wavelengths from about 400 nm to about 1200 nm being most preferred. Simultaneous or sequential use of multiple lasers of different wavelengths that have been selected to optimize different interactions with probes or targets is also possible.

The instrument may be contained within an enclosure that is of a size and shape suitable for mounting on a movable frame or cart commonly found in medical environments. Generally, a cart for mobile medical and diagnostic devices may be made small enough to occupy space besides a patient bed or operating room. For example, the cart with the mounted instrument may be on the order of 26", on the order of 26" long, 18" wide and approximately 32" high (waistheight), with four wheels for mobility, or smaller. The enclosure for the HOT system and microscope should easily be accessible for routine maintenance and modification of internal components. The user interface components may be mounted as appendages to the base enclosure system and interconnected by flexible conduits or with wireless transmission technology. The compact system has microscope imaging capabilities and includes an objective lens, camera and necessary tube lenses.

The system provides illumination capability for the sample under study. Illumination for bright field microscopy, fluorescent microscopy or both may be provided. The system may contain a bright field illumination capability in which the light source is above the sample to illuminate the entire relevant field. Such a light source may be incorporated directly into the enclosure housing. For fluorescence microscopy, the fluorescent light source may be contained within the enclosure housing and arranged to provide illumination from beneath the sample, or could be overhead, e.g. diodes associated with a hinged lid of the instrument. Other imaging modes including those commonly used in microscopy may also be implemented.

Focusing of the microscope objective and of the HOT components is controlled from a central source to facilitate easy operation by the end user. A sample stage, upon which as sample holder is manually or automatically loaded, provides controlled movement in at least in the X and Y axis. The motion of the stage can be motorized and controlled from a central source. It is anticipated that the system should accommodate sample slides that are one inch by 3 inches and 2 inches by 3 inches. The slide thickness may range from 1 mm to 3 mm. However, it should be appreciated that the system and staging can be configured to accept other sizes and configurations of sample preparations, including a cartridge 400 of FIGS. 9-13. To keep the system enclosed, an access port or sample door may be provided that can be opened by the user for installation of the sample onto the stage then closed prior to system operation. An automatic z-axis adjusting mechanism may automatically sense the different thicknesses of various sample plates and then automatically correct for the thickness difference by adjusting the distance of the stage to the objective lens. An automatic z-axis adjusting mechanism may be used to roughly identify the where the surface of the cartridge 400 lies. Then an imaging process routine may be used to analyze a series of brightfield images at different heights to identify particles of interest in a given area and set the final stage height prior to HOT activation.

All laser sources associated with the system are enclosed within the cabinet housing. It is envisioned that at least one laser will be used for the HOT system, but additional lasers may be provided for manipulating the samples, providing illumination, or monitoring focus. The lasers and any necessary transmission conduits all should be contained within the mobile cart and preferably within the enclosure housing/cabinet of the system. The instrument also includes a computer system configured to control the HOT system, motorized focusing systems, auto-focusing systems and user interface components. The computer system may employ easy to use software such as Microsoft Windows and National Instruments LabView software systems. Power requirements for all electrical components of the system may be provided from a single power cord compatible with any electrical wall outlet used in a particular geography. For example, the power cord may interface with electrical supply at 110 volts and at 15 or 20 AMPS. Because the instrument is compact, mobile and easy to use, it may be hosted in traditional health care or diagnostic laboratory environments.

Figure 14:
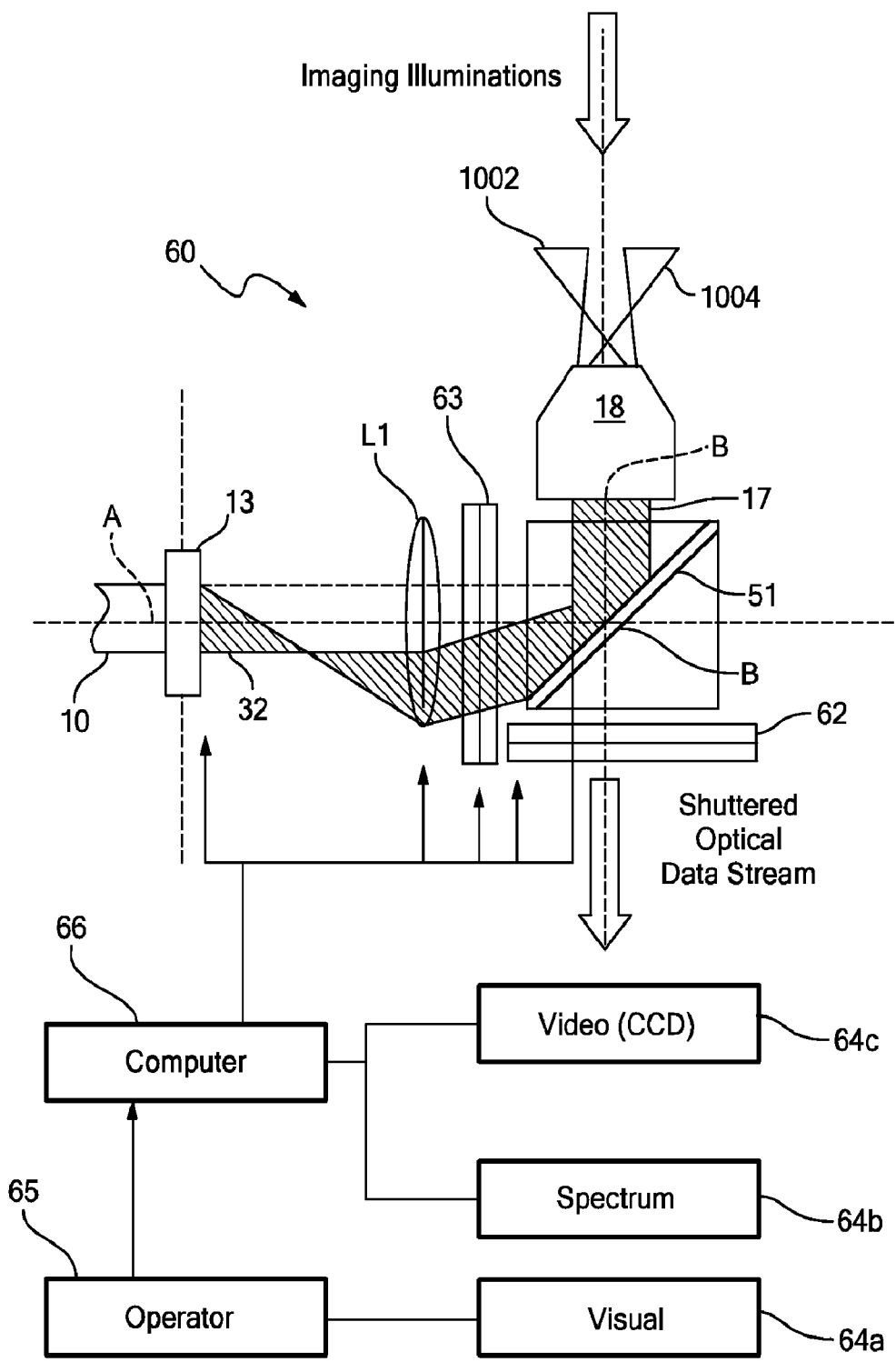
FIG. 14 schematically shows a combined HOT and microscopy instrument in accordance with an embodiment of the invention.

FIG. 14 shows a diagrammatic illustration of a HOT system with microscope and camera components. The illustration is reproduced from U.S. patent application Ser. No. 10/701,324, the entirety of which is incorporated by reference herein. The figure shows a system that is stationery due to the size and arrangements of components. This device employs a HOT component system with a YAG generating laser beam 10, which passes through a diffractive optical element (DOE) 13, a transfer optic L1 to a beam splitter 51 so that it may act on a sample positioned at area "B". Additionally the system includes imaging illumination from above, and a video camera 64C positioned below to capture images of the sample and transmit them to the operator 65. Images may be transmitted onto a video screen. This system additionally includes a computer 66 linked to various electronic components in providing controlled software for use by the operator. Such prior art systems make use of conventional microscope, laser, illumination and video camera components making it quite large. Each component sub system requires a relatively stable mounting surface, which heretofore has required assembly of such systems in a stable, workbench environment.

Figure 15:
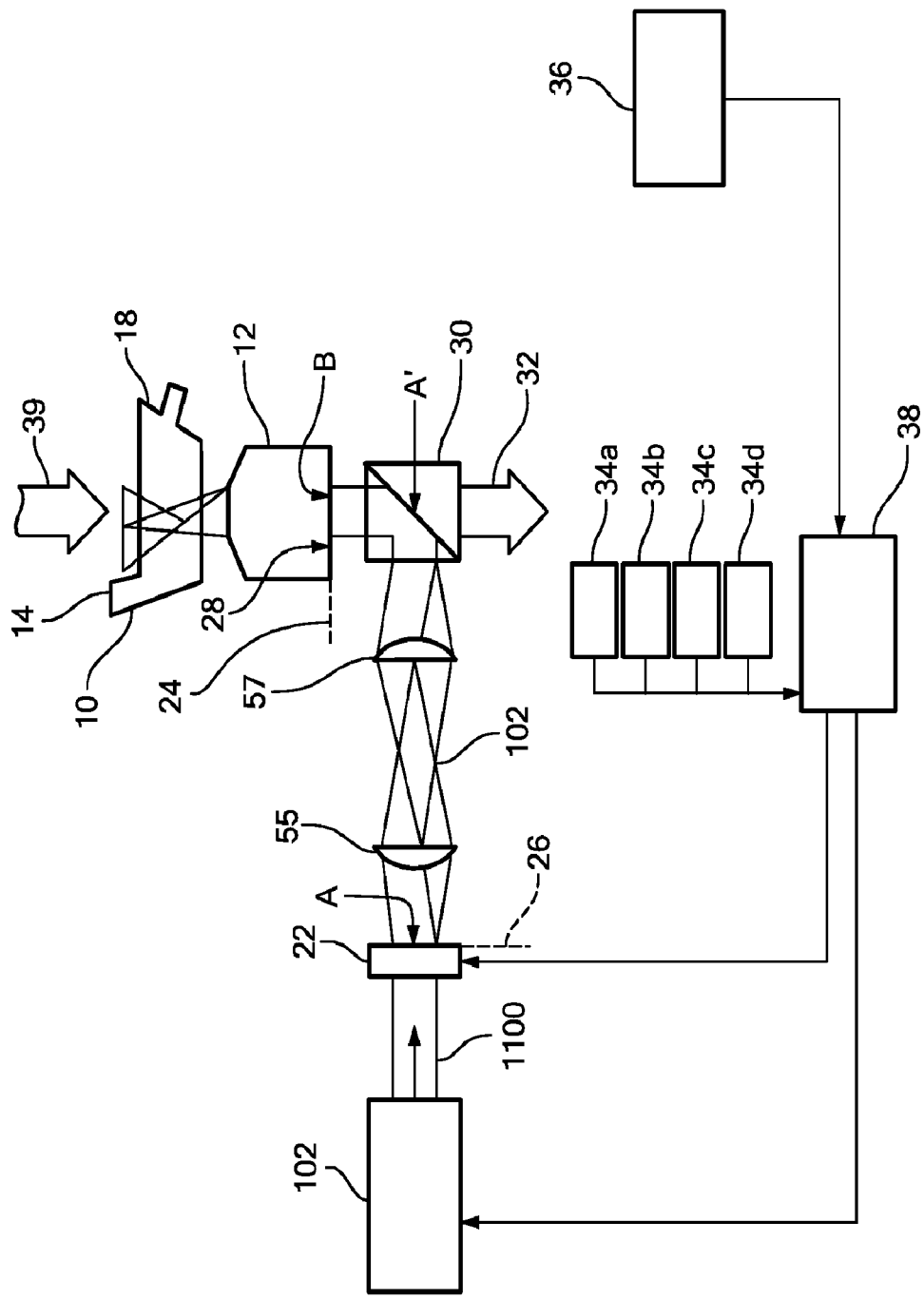
FIG. 15 schematically shows an alternate combined HOT and microscopy instrument in accordance with an embodiment of the invention.
Figure 16:
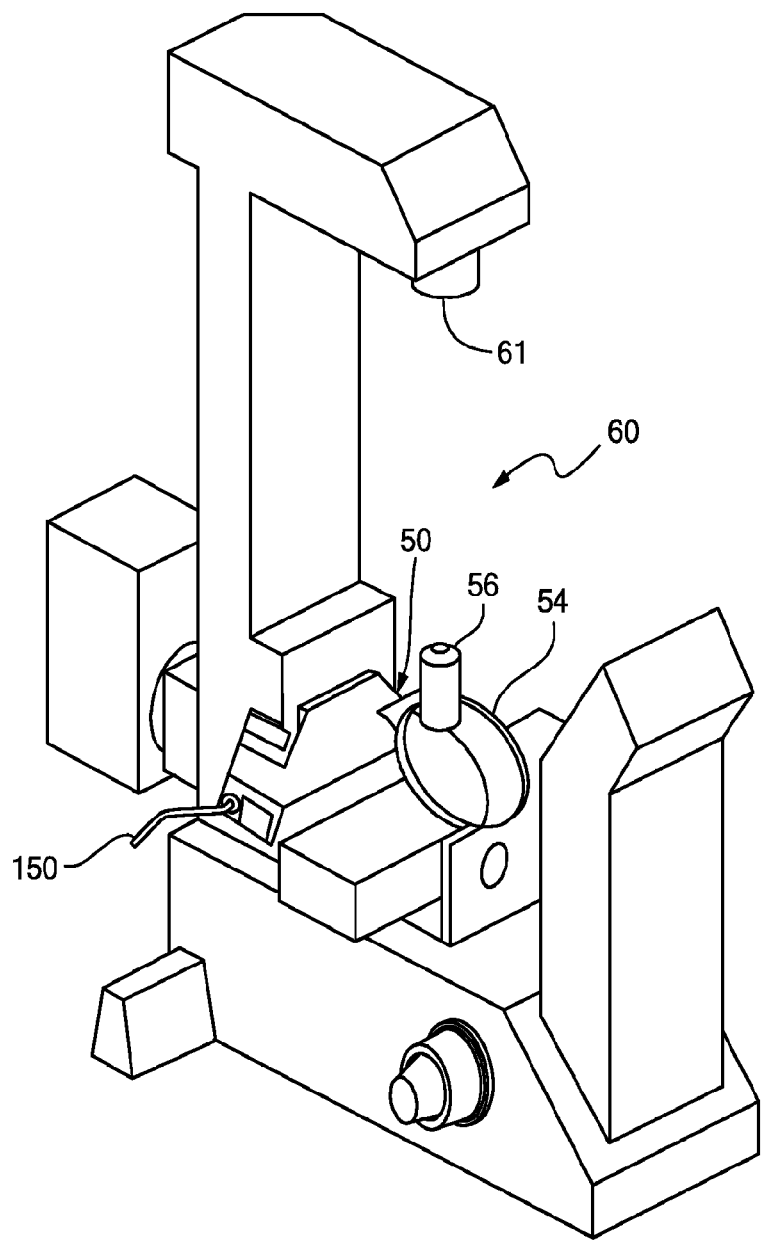
FIG. 16 is a perspective view of a microscope for use with the embodiments of FIGS. 14-16.
Figure 17:
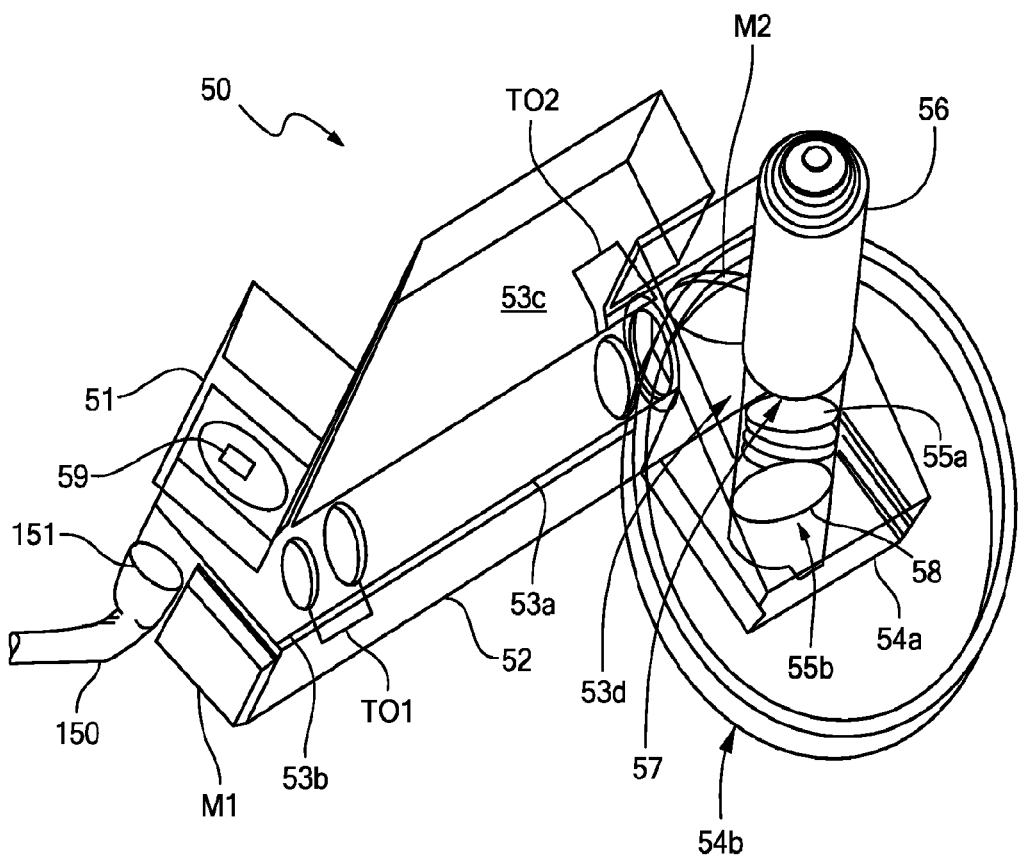
FIG. 17 shows a perspective view of a HOT subsystem for use with the embodiments of FIGS. 14-16.

Another HOT system and microscope combination is shown in FIGS. 15 through 17, reproduced from U.S. patent application Ser. No. 09/886,802, the entirety of which is incorporated by reference herein. As shown schematically in FIG. 2A, the system components are similar to that of the previously-described system. A HOT laser 102 generates a beam 1100 to a beam splitter 30 directing the beam toward an optical element 22 and through the back aperture 28 of a focusing lens 12 to analytes in a vessel 10. A major part of that system is the microscope which is shown in FIG. 16. The microscope 60 is large and stationary to provide a housing for the illumination source from above 61, objective lens 56 and HOT system received in the nose piece 54. The HOT laser system is joined to an external laser source through optical fiber 150. As shown in FIG. 2C, the HOT sub-system 50 provides a housing 52 to carry several mirrors and one and then two, transfer lenses TO1 and TO2, an optical element 51, light channels 53A and 53D and beam splitter 58.

Joined to the microscope 60, but not shown in these figures, are additional components such as the computer, camera, sample stage, movement and focusing mechanisms and laser generators. The plurality of complex subsystems that must be interconnected around the traditional scale of microscope 60 may make the entire system immobile.

Figure 18:
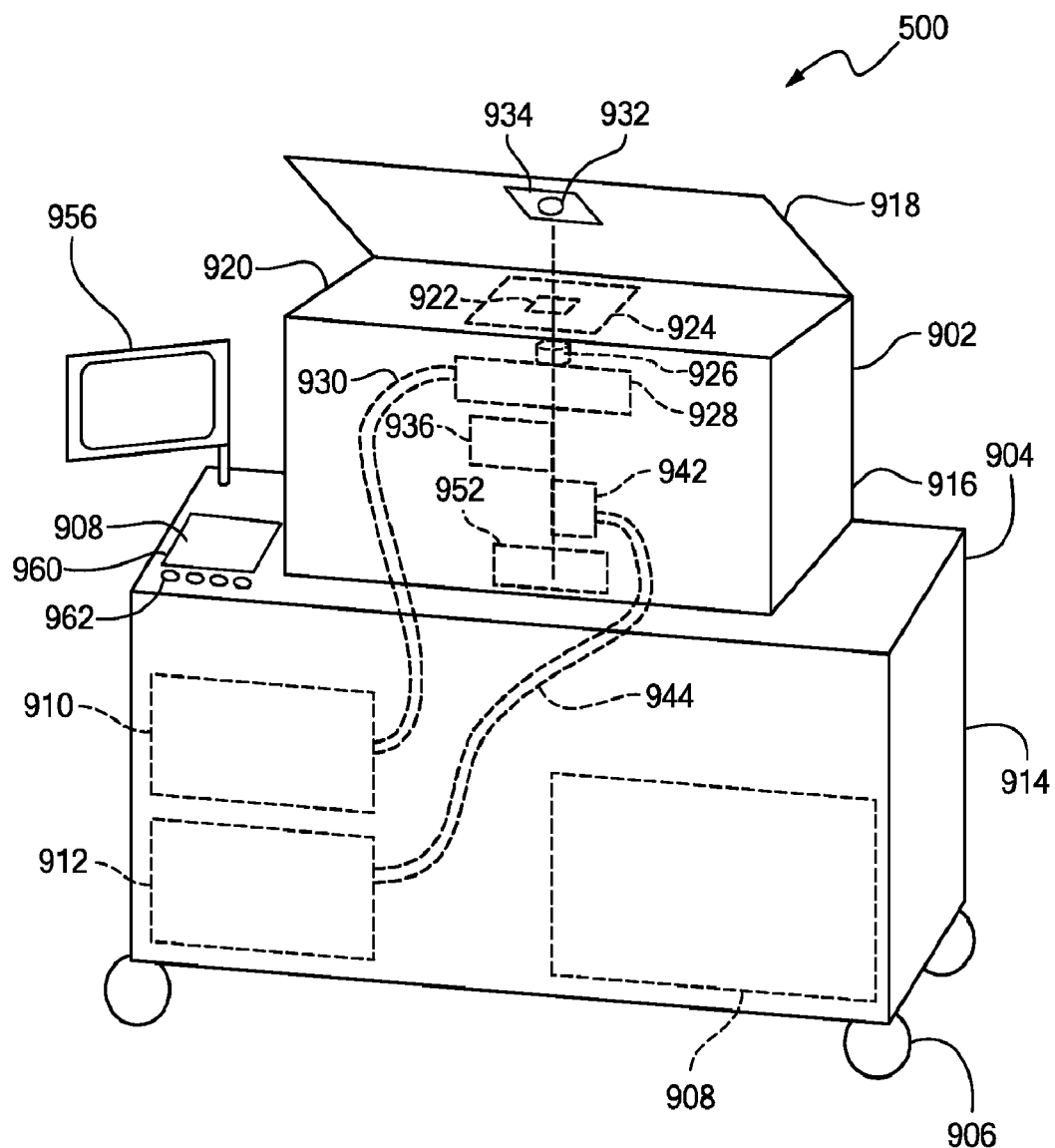
FIG. 18 shows a schematic view of a compact, mobile, combined HOT and microscopy instrument in accordance with an embodiment of the invention.
Figure 19:
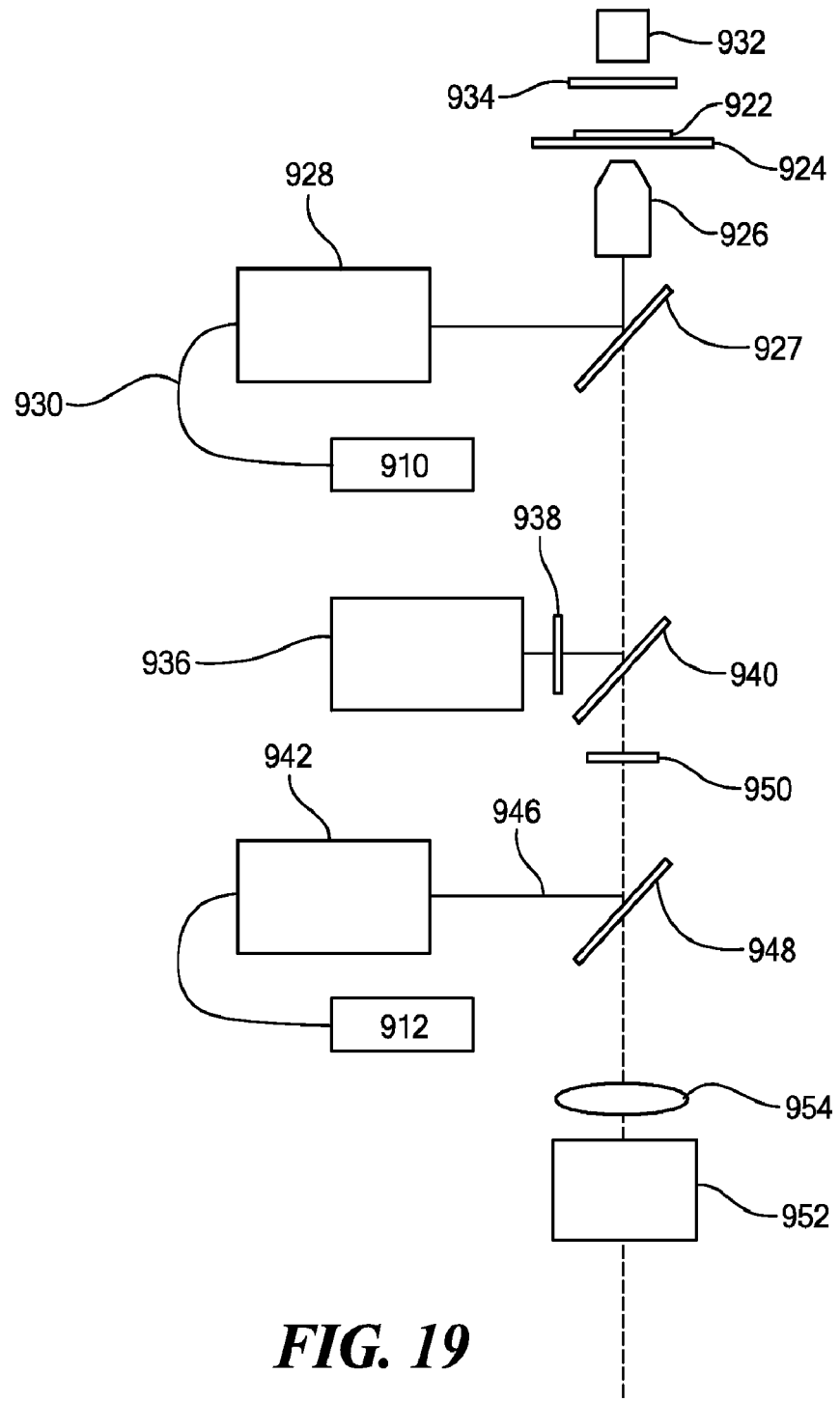
FIG. 19 schematically shows components of the instrument of FIG. 19.

A compact and mobile HOT microscope instrument 500 in accordance with an illustrative embodiment of the present invention is shown in FIG. 18 and a schematic illustration of the component parts is shown in FIG. 19. The instrument 500 comprises an enclosure 902 for housing working components of the instrument. The enclosure may be made from any rigid material that is lightweight and durable and capable of preventing transmission of laser light at the wavelengths used for HOT. The enclosure preferably is positionable on or is part of a wheeled structure 904, e.g., a cart. The cart 904 should have at least two wheels 906 and preferably four wheels for stability.

The instrument 500 may be configured such that larger electrical components such as a computer 908 and laser generators 910 and 912 and any other large electrical components, such as power supplies, may be positioned in a bottom section 914 to maintain a lower center of gravity for added stability of the mobile cart. Such components may not need to be enclosed if they do not emit outwardly the laser light. Light emitting components that should be enclosed due to safety concerns, optical transmission requirements, finite movement capability or admission of laser light may reside in an upper portion 916 that is enclosed by the enclosure 902. The enclosure 902 may be configured to have a closable opening, such as a lid 918 through which a user can access the internal components of the instrument 500 and place a sample cartridge 400 to be handled by the instrument. Alternately, a tray may automatically extend from the instrument 500 and retract to accept a cartridge 400 and properly position it for analysis. Other mechanisms for loading sample cartridges into instruments may also be employed, as is known in the art, including turntable mechanisms and spring-loaded slots. The opening 920 that is protected by the movable cover 918 should be sufficiently large so that an operator can place a sample cartridge 400 in a sample area 922 of the sample stage 924. The cover 918 should include a kill-switch so that the device cannot be unsafely operated while the cover is open. The sample stage 924 is positioned immediately beneath the cover. The stage system may be a Prior Proscan II Controller with H117 XY stage for Nikon TE2000U and focus knob collar. The stage 924 and focus knob may have encoders. An objective lens 926 is positioned immediately beneath the sample stage 924, for imaging the capture zones on the cartridge 400, and for forming the holographic optical traps. The objective lens 926 may be a Nikon CF1 Plan Apo 40X Air NA=0.95, WD=0.12-0.16. The objective turret may be a Nikon TE 200 turret.

The HOT sub-system 928 is located immediately beneath the objective lens 926 and may be adapted for use from a BioRyx 200 (Arryx, Inc.). The components of the HOT sub-system, which include a Diffractive Optical Element (DOE), spot blocker, collimator and other associated lenses and relay optics, may be configured for a given monochromatic wavelength (e.g., 1064 nm) used to generate optical forces. The DOE used may be a Spatial Light Modulator (SLM), e.g., from Boulder Nonlinear Systems (Model P512-1064). The SLM may have a dielectric coating for high power handling. A Central Spot blocker may also be used for blocking the zero order reflection and high order zones from the SLM. The HOT system has an emission port directed at the sample stage. A dichroic mirror 927 may be used to direct the optical trapping light emanating from the HOT-Subsystem 928 into the cartridge 400 while simultaneously allowing other illumination and imaging wavelengths to be transmitted through the optical path.

Optical fibers 930 for connecting lasers to the laser sources may be Oz Optics fibers. The HOT laser may be a IPG 10W fiber laser with FC connector. Additionally, a collimator may be used to connect to the HOT sub-system, such as the micro laser Systems FC2O-IR-T/A. The HOT sub-system also has connections (not shown) to the computer 908 for controlling the diffractive optical element.

Other components, including illumination sources may be included within the enclosure 902. One illumination method for the compact system uses a bright field illumination source 932. To provide illumination from above the sample area 922, one compact configuration for the bright field illumination 932 is to locate it in the movable cover 918, as shown in FIG. 18. Such a bright field illumination 932 may comprise an LED light source that outputs a wavelength of approximately 525 nm with a diffuser 934 to ensure uniform illumination.

An alternative illumination source, or preferably an additional illumination source may comprise a fluorescent excitation illuminator 936 positioned below the sample area 922. The fluorescence excitation light is transmitted through an excitation filter 938 to a dichroic mirror 940. The fluorescent illumination may be part of a sub-assembly such as an an Exfo Excite illuminator coupled to an epifluorescent cube (e.g., a DAPI-FITCTR in TE2000U cube (Nikon). Alternatively illumination sources for fluorescence excitation could also be incorporated into the enclosure 902 located above the sample area within the cover 918.

Another optional component sub-system is a laser alignment guidance system (LAG) 942 for assisting with auto focusing of the stage 924 relative to the objective lens 926. The LAG alignment laser 942 may be a diode operating at 635 nm. The laser may be powered by a separate, remote laser source 912 and the laser light may be transmitted through an optical fiber 944 into the main enclosure 902. Alternately, the laser 942 may be small enough to fit directly within the 902 enclosure. The alignment laser 942 delivers a laser beam 946 either directly or through a light guide 944 (e.g., a fiber optic) to a beam splitter 948 such as a dichroic mirror, which then transmits the laser energy through an emission filter 950 preceding the sample stage objective area.

Another sub-system component that assists usability of the system is a camera 952 for collecting and transmitting images of the sample for analysis by the common computation assembly 540 or to an operator of the device. The camera may be a charge couple device (CCD) or the equivalent. The camera is preferably mounted in the enclosure 902 so as to be aligned with the positioning of the sample area 922 of the sample stage 924. Part of the camera optics may include a tube lens 954 to focus images onto the camera surface. An example of a suitable camera for the system is a Qimaging Retiga Exi color cooled. Video output may be viewed on a computer display 956, which may also display other control, monitoring and data analysis features The system may be controlled through a user interface 960, which may comprise an LCD user interface screen 956 for presenting text to the user and may offer touch screen capability. Alternatively, the user interface 960 may offer several push button controls 962 to begin automotive processes of the system. An additional alternative, not shown, may be a computer keyboard for directly interacting with software residing on the computer that is capable of controlling the various sub-systems of the invention.

All sub-systems and individual components of the compact HOT/microscope system may be attached to the wheeled structure by conventional mechanical fasteners known in the art. Additionally conventional damping systems may be added.

Figure 20:
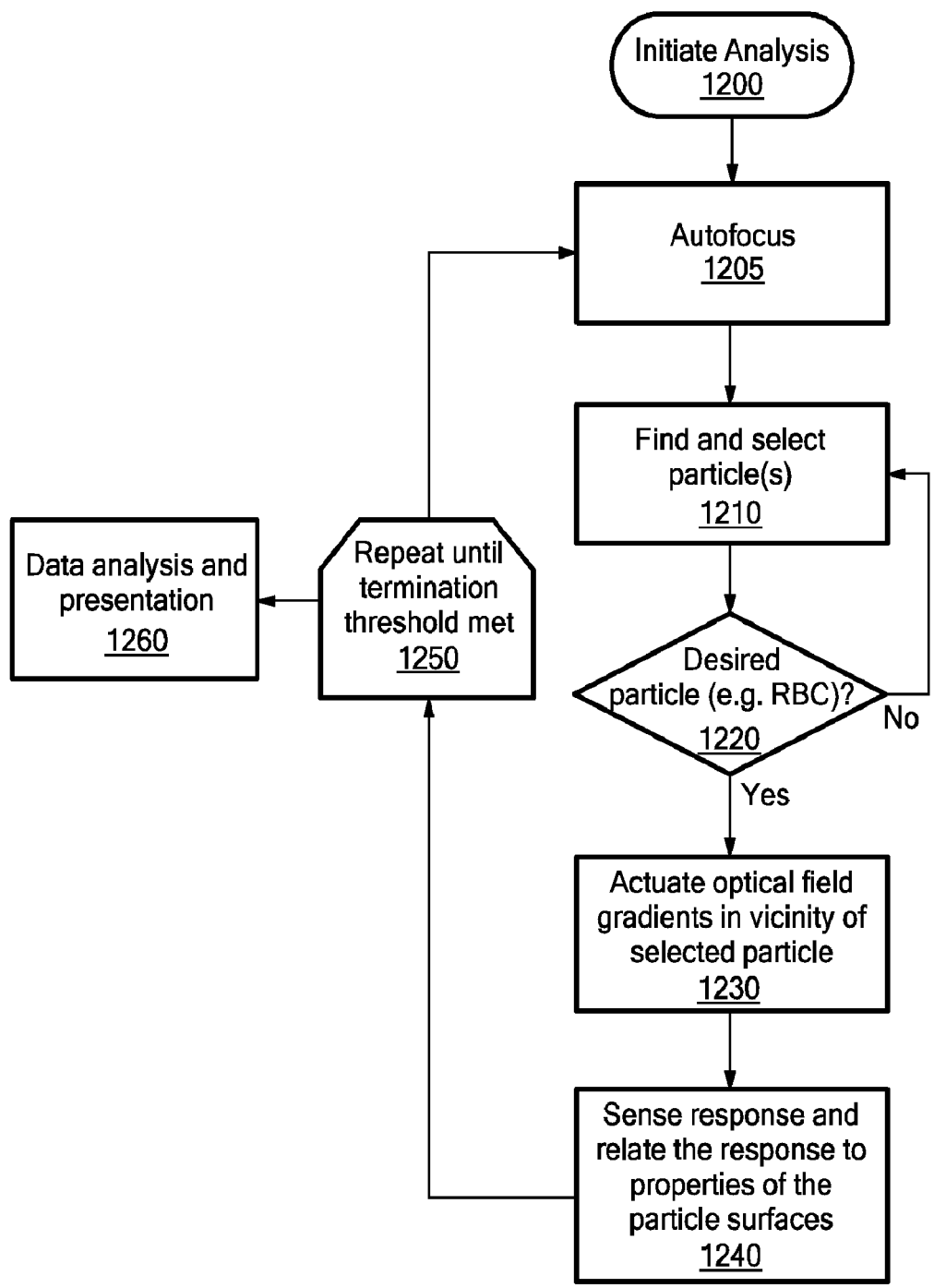
FIG. 20 is a flow chart for a software implementation for executing the method of FIG. 1 on an automated instrument.

The instrument 500 of FIGS. 8 and 18 may be capable of highly automated operation. FIG. 20 is a flow diagram for an illustrative control scheme to be implemented on an instrument 500. Although described in a serial manner, many or all of the operations of this embodiment may be performed by the instrument 500 in a parallel manner on multiple particles. After loading a sample onto a cartridge 400 and mounting the cartridge into the same area 922, and after allowing the particles to settle and contact the capture zones 210, analysis may be initiated. Analysis may be initiated (step 1200) manually by pressing a button (physical or via a GUI). Alternately, the microscope assembly (item 520 of FIG. 8) may, in conjunction with the computation assembly (item 540 of FIG. 8), detect the presence of a cartridge 400, track the particles to determine when the particles have completed their settling phase, and then initiate optical force analysis. If necessary, additional time may be allotted to for further binding of the particles to the capture zones 210. The temperature of the cassette may also be automatically controlled to optimize binding or to ensure consistent results. The instrument will automatically focus on the capture zone (step 1205). The instrument will then automatically find one or more particles and then select one or more of these for immediate analysis (step 1210). Optionally, the instrument will image the particle to determine if it meets a specified set of criteria (1220). For example, in a blood typing analysis, optical forcing of lymphocytes would wasted time at best, and at worst, would skew the results if the lymphocytes were not distinguished. The instrument may use pattern recognition routines, size and shape data (e.g., detection of objects within a specified appearance range for a red blood cell or other particle) absorbance data (e.g., detection of red color in a red blood cell), fluorescence microscopy data (e.g., presence of a dye or labeled antibody), other spectral data or other non-spectral measurements to make this determination. The instrument will then automatically actuate optical field gradients (step 1230) in the vicinity of the selected particle to apply a potentially displacing force to the particle. By continuing to image the particle during and/or after application of the force, and thereby sensing any displacement of the particle in response to the force (step 1240), the affinity or avidity of the capture zone for the particle may be determined. As described above, since capture zones contain probes that specifically bind target analyte species, the presence of these analytes on the surface of the particle may be determined. For subsequent analysis, the instrument will record, in computer memory, the location of each particle analyzed in terms of which capture zone it was associated with. The identity of the capture zone may be determined from machine-readable markers, from knowledge of the cartridge orientation with respect to reference markings (the cartridge may also be keyed for insertion in a particular orientation), or other method. The selection and analysis of particles is repeated with an optional autofocus step, until a termination threshold is met (step 1250). The threshold may be, for example, a given number of particles analyzed in total, a given number of particles analyzed in each capture zone, elapsing of a maximum time, or surpassing a statistical measure of error (e.g., achieving a standard deviation below a specified value). Additionally, multiple fields of view may be sampled, either within a single capture zone 210, or in multiple capture zones 210. In order to compensate for positioning errors, an autofocus routine may bee execute with each change in field of view. The data is then analyzed and presented to the user (step 1260). In the case of blood typing or other clinical use, the analysis may include the blood type or other clinically relevant semantic value.

Figure 21:
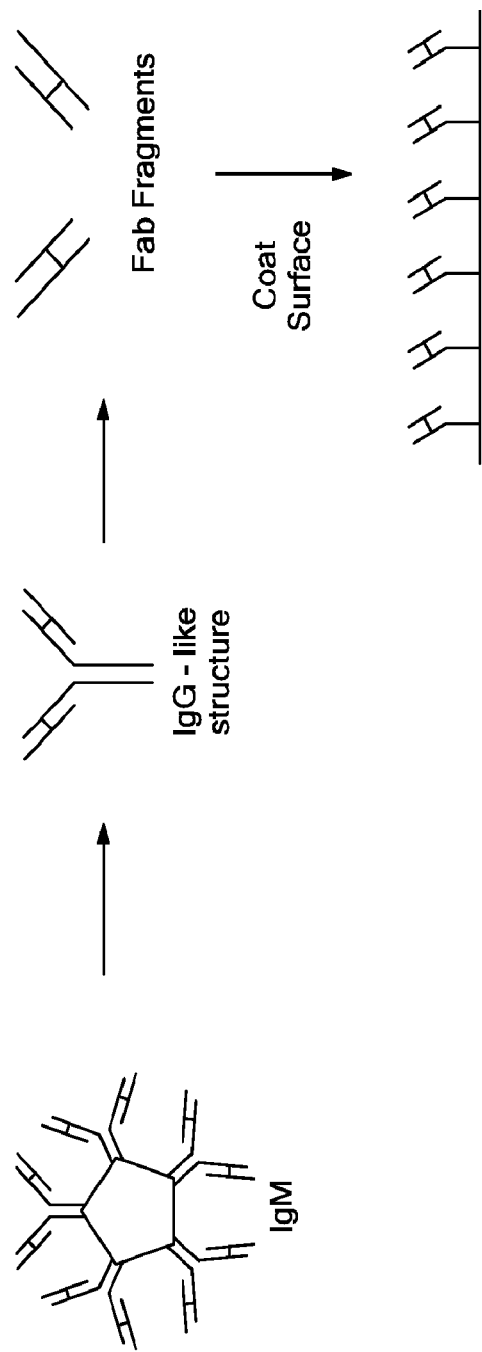
FIG. 21 is a reaction scheme for fragmenting IgM antibodies to produce coated capture surfaces.

FIG. 21 schematically shows an embodiment that includes a method for coating a surface, such as a capture zone 210 with antigen-binding protein fragments derived from IgM's. A solution containing IgM molecules is treated with a disulfide reducing agent such as 2-mercaptoethylamine HCl, dithiothreitol, or 2-mercaptoethanol. For Example, the ImmunoPur IgM Fragmentation Kit from Pierce Biotechnology (Rockford, Ill.) contains instruction and reagents for various cleavage methods. These reactions can produce antibody fragments with specific molecular weights by controlling the reduction time, temperature, and relative concentration of the reducing agent. These fragments may then be immobilized on a matrix such as a glass or quartz slide, a particle, a three dimensional structure, a resin, or gel. The resulting matrix will then have a specific affinity for the antigen recognized by the IgM. In one embodiment, the matrix is a glass slide or a region of a glass slide. Immobilization may be performed using various coupling chemistries, several of which are available from Pierce Biotechnologies (Rockford, Ill.). For example, Sulfosuccinimidyl 4-[N-maleimidomethyl]cyclohexane-1-carboxylate (Sulfo-SMCC) may be used to crosslink sulfhydryl groups on the fragment to an amino-silane on a glass matrix. Multiple such matrices (regions located on independent structures or co-located on adjacent or non-adjacent regions of a continuous structure) may be coated with fragments to produce regions of varying affinity. A cell may be exposed to the multiple regions. By observing parameters related to the strength or relative strength of the interaction between the cell and the surface, an antigen on the surface may be identified. In an embodiment, the cell is a red blood cell and the antigen-specific binding regions recognize blood types.

As mentioned previously, the methods and apparatus described above may be useful not just in blood typing, but in many other types of biological, biochemical and chemical analytical procedures. For example, instead of analyzing red blood cells, one may analyze lymphocytes, cultured cells, bacteria, biopsy sample, and the like. One or more types of probes may be used in each capture zone; for example, a capture zone may have a mixture of three antibodies that when combined impart specificity for a certain type of stem cell or cancer cell. Tests for syphilis, HIV or hepatitis B cell surface antigens can be envisioned using the same type of protein binding ligand assay. Cells to be analyzed can be purified before use (e.g., using fluorescence activated cell sorting). Furthermore, many different samples can be tested on a single substrate, or many different tests of a single sample can be tested on a single substrate.

Although there are numerous types of assays that may be performed with embodiments of the present inventions, a large number of these fall into the following three categories described below: direct assays, indirect assays and competitive assays.

Figure 22A:
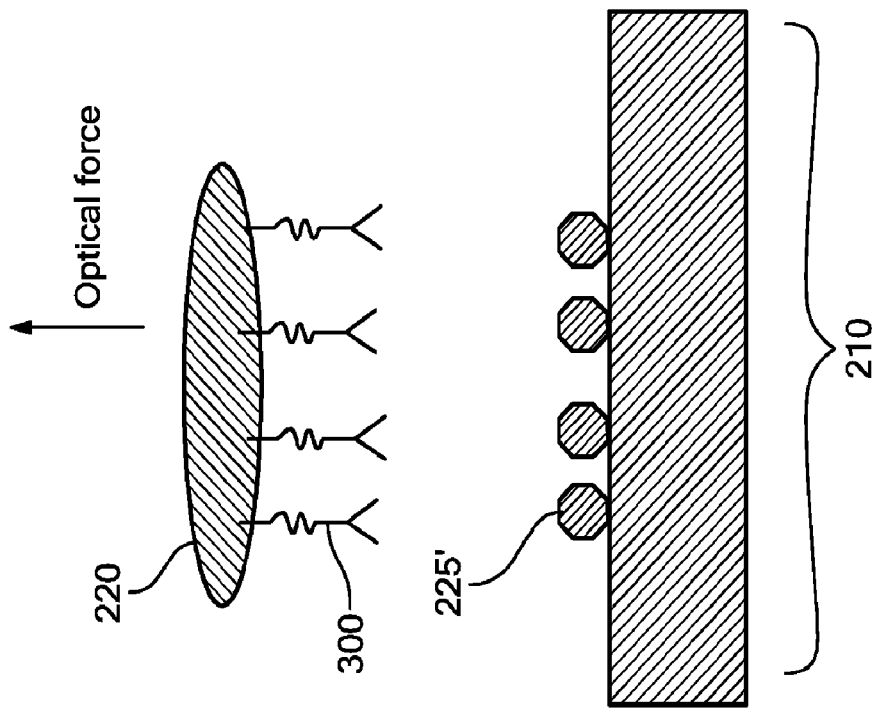
FIG. 22a is a schematic showing an assay in accordance with an embodiment of the invention in which analyte antigen is coupled to a substrate and recognized by a particle-labeled probe.
Figure 22B:
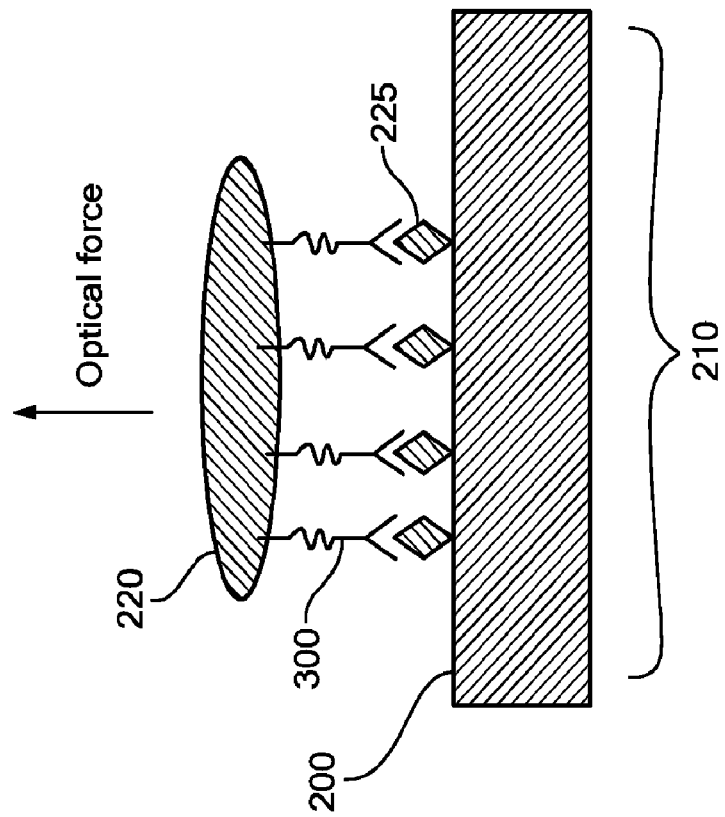
FIG. 22b is a schematic showing the assay of FIG. 22a in which the antigen is not recognized by the probe.
Figure 23B:
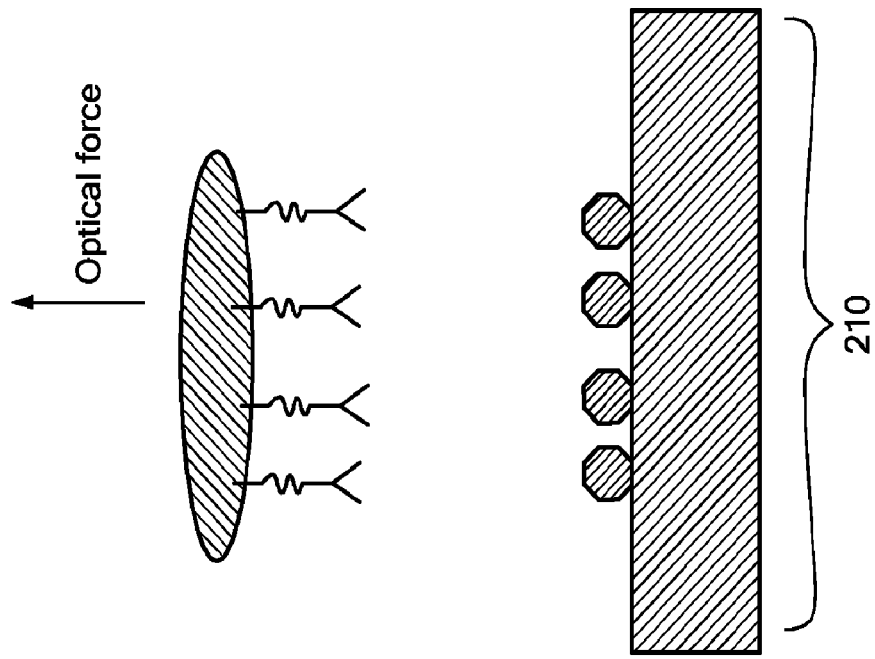
FIG. 23a is a schematic showing an assay in accordance with an embodiment of the invention in which analyte antigen is coupled to a substrate and recognized by a complex of an antibody and a particle-labeled probe.
Figure 23A:
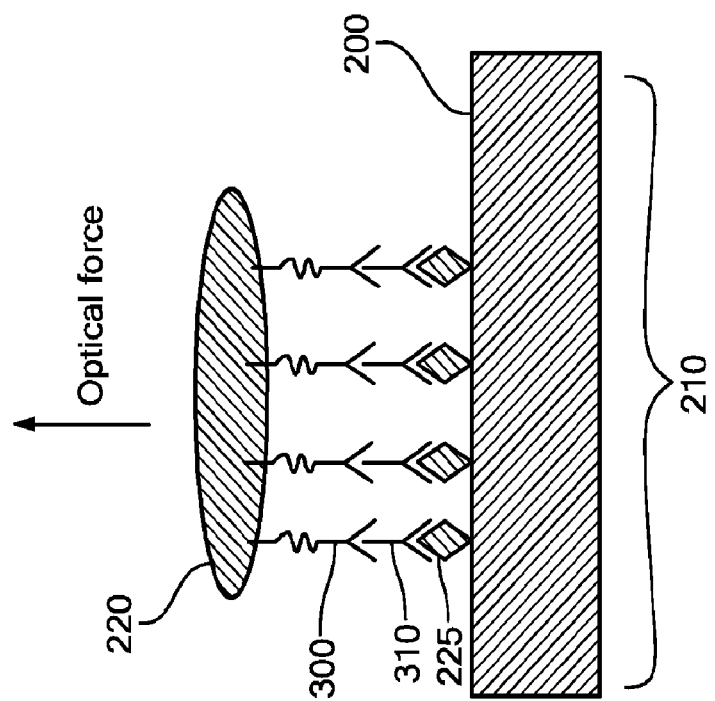

A direct assay involves performing an observation of a parameter related to how a directly labeled probe molecule interacts with a target. In embodiments related to observation of responses to optical forcing, the label may be an optically active substance, such as a particle. For example, a 1-100 micron diameter glass or plastic bead with immobilized antibodies may be used to probe a target analyte that is specifically or nonspecifically bound to a substrate. The analyte may be covalently or noncovalently attached to the substrate. The probe and label may also be combined into a single biological entity; e.g., a natural or genetically engineered cell expressing a surface protein that acts as a probe. For a blood typing assay, red blood cells could be adhered to a surface using an antigen common to all red blood cells, particles carrying blood-type antigens contacted with the red blood cells, and the responsiveness to optical forces of the bound particles used as the parameter to characterize the cell surfaces. FIGS. 22a and 22b show an example of a direct assay. An analyte antigen 225 is bound to a capture zone 210 and a particle 220 with immobilized antibody probes 300 is contacted with and bound to the capture zone 210. The strength of the binding interaction, if any, is determined using application of optical force, as described above. If the antibody 300 recognizes the antigen 225, as is shown in FIG. 22a, then a higher force is required to displace the particle 220 than is needed in the alternate scenario, shown in FIG. 22, in which the antibody 300 does not recognize a non-binding antigen 225'. Alternately, the target may be an antibody and the probe on the particle may be an antigen.

Contrastingly, an indirect assay involves detecting a property of a second probe that is bound to the first probe. Like the direct assay, the parameter may be optical forcing of the second probe, if the second probe is suitably labeled. The second probe may be specific for either a chemical moiety of the first probe, or for a label of the first probe (particulate or otherwise). In the example illustrated in FIG. 23a, unlabeled monoclonal mouse antibodies 310 may be used as a first probe and contacted with immobilized target antigen 225 (e.g., directly immobilized on substrate 200 or integral to an immobilized cell), the second probe may be a particle 220 labeled with attached probe moieties 300 that are polyclonal rabbit anti-mouse antibodies. The second probe particles 220 may be contacted with the first probe antibodies 310, allowed to bind, and tested for specific binding interactions by observing responses of the particle to the application of optical forces. As shown in FIG. 22b, lack of a specific binding reaction allows displacement of the particle 220 at a lower optical force level. In another example, HIV (human immunodeficiency virus) antigen is attached to a substrate. The substrate is exposed to patient serum. If HIV antibodies are present, they will bind to the HIV antigen on the substrate. The patient serum is removed by washing with buffer, leaving specifically bound antibody substantially undisturbed. A particle-labeled antibody specific towards human antibody (e.g., rabbit anti-human IgG) is introduced and tested for specific binding via optical force application. This type of assay is particularly advantageous in the context of multiplexing because only one, or only a few types of particle labeled probes may be used to detect a far greater number of analyte molecules. For example, a variety of antigens to human pathogens may be immobilized in separate capture zones and an antibody-containing patient sample (e.g., blood or serum) added in such a manner as to cause fluid communication between the multiple zones. After allowing sufficient time for antibody binding, a solution of particle-labeled anti-human antibodies (e.g., anti-IgG, anti-IgM, anti-IgG, and IgA or a combination thereof) may be added and allowed to bind ti the captures zones. Optical forcing (including parallel optical forcing) may then be used to probe the response of the particles to reach conclusions about the patient's past pathogen exposure or immunization state. Such techniques may be applied to several, 10s, or even 100s of antigens in parallel using between one and 4 labeled particle types. Because so few particle types are needed, it is relatively simple to tag each of the particle types, for example, with fluorophores of differing excitation or emission wavelengths, to deconvolve the results. In another example, a patient's antibody profile may be determined with respect to numerous antigens for the purposes of diagnosing an allergy.

Figure 24:
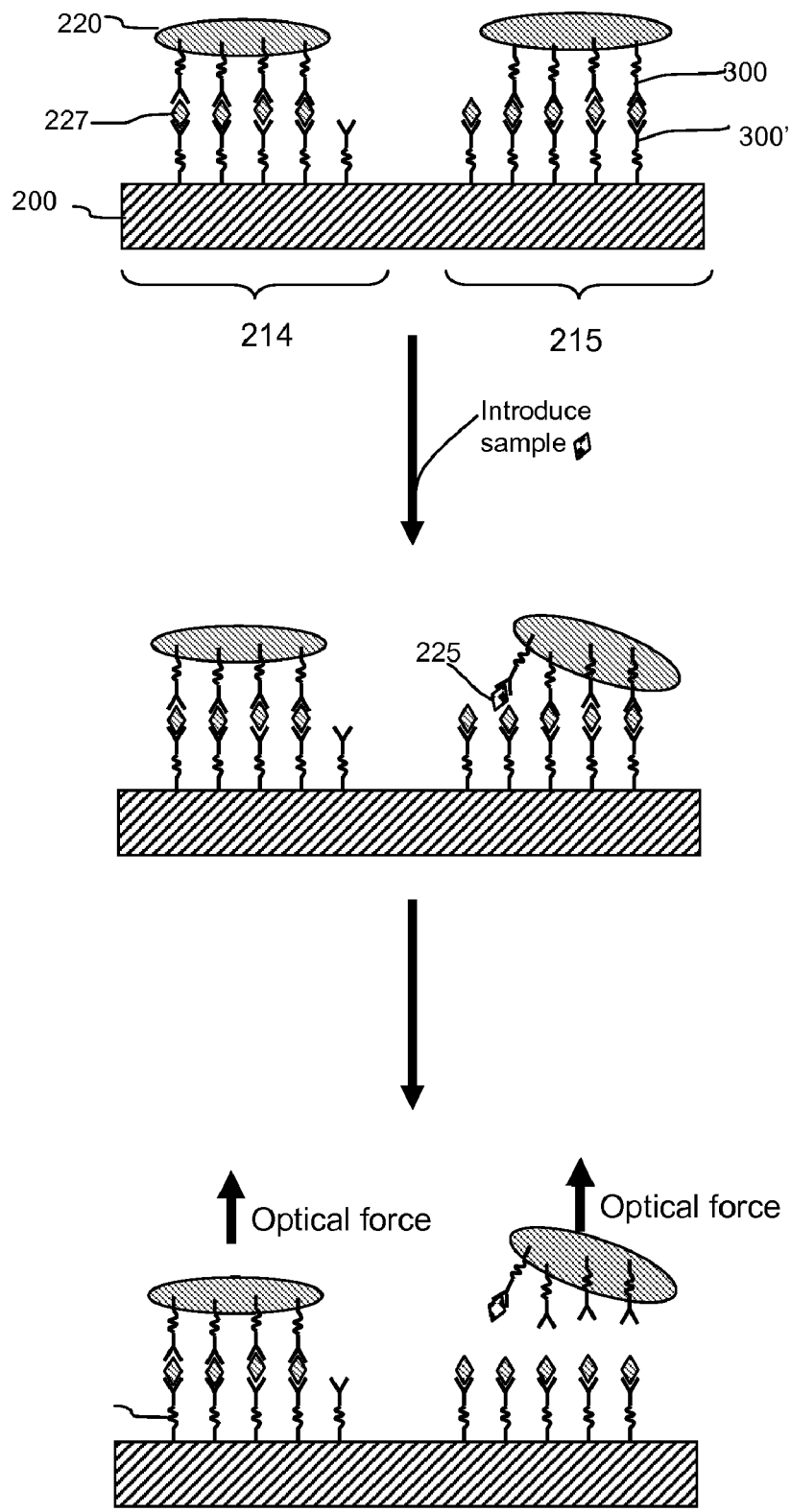
FIG. 24 is a reaction scheme showing a competitive assay according to an embodiment of the invention in which the binding force between a particle and a capture zone is decreased upon introduction of a sample.
Figure 25:
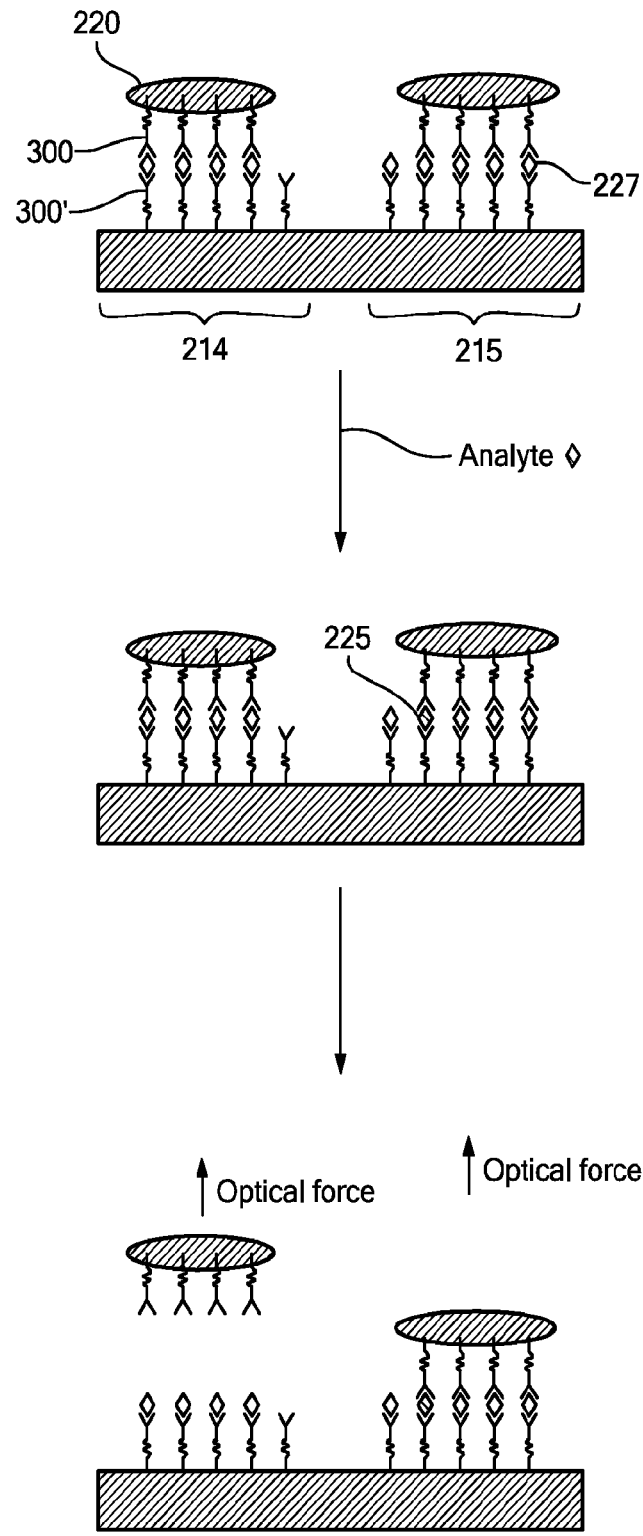
FIG. 25 is a reaction scheme showing a competitive assay according to an embodiment of the invention in which the binding force between a particle and a capture zone is increased upon introduction of a sample.

Competitive assays involve detecting an event associated with displacement of a bound analyte or reporter or other molecule. U.S. Pat. No. 5,620,857 to Weetall, et. al., incorporated herein by reference, discloses a method for performing a competitive immunoassay using optical tweezers. However, the disclosed assay is performed in a serial manner at best, yielding fewer data points. Accordingly, little information may be gained in a given time and correspondingly lower confidence results will be obtained. Contrastingly, the competitive assay embodiments described herein may be performed in a parallel manner; e.g., by testing multiple particles concurrently using HOT. As a result, more data points may be obtained for higher-confidence results and/or more types of targets may be tested. FIGS. 24 and 25 illustrate some assay configurations that use optical force with competitive binding.

As shown in the reaction scheme of FIG. 24 ternary sandwich structures are formed at the captures zones 214 and 215. The sandwiches are comprised of substrate-bound probes 300', placeholder molecules 227, which are covalently immobilized on capture zones of the substrate and particle-bound probes 300, covalently immobilized on particles 220. The placeholder molecules 227 may have a binding potential for the probes 300 and 300' that is at least identical or similar to that of analyte of interest in the target sample. Capture zones 214 and 215 have probes 300, 300' and placeholder molecules that are specific for different analytes 225. For example, the placeholder may be recombinant forms of antigens of interest. Additionally, substrate-bound probes 300' may having differing affinities or specificities to various analytes of interest and may be pre-assembled as ternary complexes with suitable placeholder molecules 227 and particle-bound probes 300. When a sample is added, if analyte molecules have an affinity for the probes 300 and 300', they will tend to displace the placeholder molecules 227, given a suitable time to approach equilibrium, to a degree that depends on relative binding constants and mass action. If the particles 220 and capture regions interact in a polyvalent manner, under intermediate concentrations of analyte 225, only some of the placeholder molecules will tend to be competitively displaced. These intermediate states will be detectable as differences in the amount of optical force required to displace a particle.

FIG. 25 shows a reaction scheme for a competitive assay in which the placeholder molecules 227 have a lower affinity for the probes 300 and 300' than the analyte molecules 225. Capture zones 214 and 215 have probes 300, 300' and placeholder molecules that are specific for different analytes 225.

As a result, if the placeholder molecules are competitively displaced by target analyte 225 from the added sample, the binding interaction between the capture zone 215 and the particle 220 will be increased and this may be detected as an increase in the optical force needed to displace the particle. If a capture zone 214 has an affinity for a non-cross-reacting analyte, binding forces for sandwiches in this zone will be unperturbed. As with the other assay embodiments, this process may be performed in a parallel manner on multiple particles (e.g. 3, 5, 10, 100 or more).

In alternate embodiments of the competitive assays of FIGS. 24-25, the target sample may be added in a way that it contacts only one target zone at a time, or contacts multiple target zones. For example, the capture zones may be in individual, substantially isolated wells of a sample holder and the sandwich structures created by adding appropriate placeholder molecules 227 to capture zones with substrate-bound antibodies 300', washing, adding particle-bound probes 300, and washing again. The structure is then ready for use.

However, the situation becomes significantly more complicated if the capture zones are simply regions on a single substrate within a single fluidic structure. In this case, added fluids will communicate with multiple capture zones. As a result, the placeholder molecules may need to be incubated with the capture zones for an extended period of time to allow them to sample multiple probe types and dock with the appropriate probes. Because the particles 220 tend to be massive enough to settle, they will tend not to visit multiple capture zones 210. To overcome this, particle-bound probe solutions may be dispensed directly atop the appropriate capture zones 201. To prevent spreading and cross-reaction, temporary well structures may be formed. The temporary well structure may be a pipette tip pressed against the substrate for a period long enough to settle. Alternatively, an array of through-holes may be contacted with the substrate, the particles dispensed and allowed to settle before removal of the through-hole array. In yet another alternative embodiment, the capture zones are located in small depressions of the substrate and a volume of particle-containing fluid is added that is smaller than the volume containable by the well (accounting for surface energy effects that may allow a positive meniscus) is added. Larger added volumes of reagents and samples will flood the multiple depressions and access all the capture zones.

In any case, the resulting fluid-communicating sandwich array structures may be used for competitive binding analysis of multiple analytes in a solution (e.g., 3, 10, 100 or even 1000 or more different analytes may be measured). In a specific example, the sandwich array is a proteomic sensor that can detects tens to thousands of different proteins in a biological sample for diagnostic or research purposes. Dynamic range may be increased by using multiple sandwich structure types with known locations (eg., tagged or located in discrete capture zones). The multiple sandwich structures may be configured to respond in different analyte concentration ranges. For example, the relative affinity of the placeholder molecules and probes differ between multiple capture zones configured to detect the same analyte at different concentration ranges.

Example 1

Blood Typing Analysis Using Automated Microscopy and Optical Forcing

The user opens the sample door and places the sample chip inside. The user closes the door and presses "Begin Test" on the touch screen. The objective lens, and hence image plane, starts out far lower (1 mm or so) than the bottom of the cartridge cover (a coverslip). The microscope stage moves to its limits to find them and then moves to the position that should correspond to the center of the first capture zone on the sample chip. The software turns on a red autofocus laser and directs the focus knob to rotate, raising the objective lens by 100 um/s or more. The camera images are observed until the system senses a flash of red indicating reflection of the laser off the bottom surface of the coverslip. A suitable algorithm is used to determine when the laser reflection is at its peak. The autofocus laser then switches off, a green LED illumination is turned on, and the objective lens is adjusted so that the image plane is roughly in the middle of the coverslip (based on the location of the bottom surface and the expected coverslip thickness). A digital camera acquires background image that it will subtract from any subsequent images used for red blood cell identification. The focus mechanism is then directed to move the image plane up to about 20 microns below where the top of the coverslip is expected to be. The focus is then raised much more gradually and camera images are acquired of the changing image. An algorithm determines when the red blood cells have come into focus and then passed out of focus again. Once the correct plane has been passed, the focus returns to that plane and image processing is performed to determine where intact RBCs are in the sample. Based on size, circularity, and edge continuity, available RBCs are identified. Ones that are too close to others, or in regions that the optical traps cannot reach, or too close to the edge of the camera image are ignored. The remaining RBCs are tested four at a time (a limit imposed by the laser power we had available). Optical traps are placed at the center of each cell and moved 20 um at roughly 7 um/s parallel to the coverslip, but the traps are placed a couple microns above the cells so the movement the cells typically experience is somewhat diagonal from the normal to the surface.

The same procedure is repeated until all testable RBCs on the field of view have been checked. If an RBC has not remained within a short distance of its original location after the movement, it is considered stuck to the surface. Based on a binomial distribution statistical test, the software decides whether to move to another field of view on the same capture zone or whether to accept the results and move to the next capture zone. If the former, the position of the next field of view is chosen based on a spiral pattern around the starting field of view, so as to minimize movement time and maximize closeness to the center of the capture zone. Depending on the statistics, many fields of view might be checked for a single capture zone if necessary. The image-based autofocus routine is usually used every time the stage is moved to a different field of view, though if the stage had only moved within the same capture zone, the autofocus starts only 10 microns below where the RBCs are expected to be. Once the capture zone is complete, the stage moves the field of view to the center of the next capture zone and image-based autofocus is again used. Once statistics are gathered for all capture zones, the touch-screen displays the results, the LED and laser are turned off, the stage moves down 1 mm and back to the center of the first capture zone, and the user is free to open the sample chamber and retrieve the chip.

In alternative embodiments, the disclosed methods for surface analysis may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for analyzing surface properties of one or more particles each having a surface, the method comprising:
   introducing a suspension having a plurality of particles into a sample holder having at least one capture zone with a given affinity for a specified chemical species;
   contacting at least a subset of the plurality of the particles with the at least one capture zone so as to allow for binding interactions to occur between the at least one capture zone and the at least a subset of particles, the binding interactions being related to the surface composition of the particles;
   applying optical forces to at least two of the at least a subset of particles concurrently, the forces tending to cause a response of the particles, wherein the responses depend on the presence, absence or degree of binding interactions between the particles and the at least one capture zone;
   sensing the responses of the at least two particles to the optical forces; and
   using the sensed responses to determine the presence, absence, or quantity of the specified chemical species disposed between the particle surface and the capture zone.

2. A method according to claim 1, wherein the applying optical forces includes using HOT.

3. A method according to claim 1, wherein the contacting includes contacting multiple particles with a single capture zone, and the responses of the multiple particles to optical forces are sensed.

4. A method according to claim 1, further comprising:
   contacting a first particle with a first capture zone having a specific binding affinity for a first chemical species so as to allow for a binding interaction to occur between the first capture zone and the first particle, the binding interaction being related to the presence of molecules of the first chemical species disposed between the surface of the first particle and the first capture zone;
   contacting a second particle with a second capture zone having a specific binding affinity for a second chemical species so as to allow for a binding interaction to occur between the second capture zone and the second particle, the binding interaction being related to the presence of molecules of the second chemical species disposed between the surface of the second particle and the second capture zone;
   applying an optical force to the first and second particles, the forces tending to cause responses of the particles; and
   sensing the response of the first and second particles to the optical forces;
   using the sensed responses to determine the presence, absence or quantity of the first chemical species disposed between the first particle surface and the first capture zone and of the second chemical species disposed between the second particle surface and the second capture zone.

5. A method according to claim 1, further comprising identifying particles prior to applying forces to the particles.

6. A method according to claim 5, further comprising selecting a first group of identified particles, applying optical forces to the first group of particles, selecting a second group of particles, and applying optical forces to the second group of particles.

7. A method according to claim 1, further comprising repeating the process to reach a data acquisition threshold.

8. A method according to claim 1, wherein the force has a component normal to and oriented away from the capture zone.

9. A method according to claim 1, wherein the force has a component parallel to a plane defined by the capture zone.

10. A method according to claim 1, wherein the force tends to displace unbound particles to a position that is spaced from the capture zone in both a first direction that is normal to and a second direction that is parallel to a plane defined by the capture zone.

11. A method according to claim 1, wherein the response includes a dislodging of the particle from the capture zone.

12. A method according to claim 1, wherein the particle is a cell.

13. A method according to claim 1, wherein the chemical species is a cell surface antigen.

14. A method according to claim 13, wherein the particle is a red blood cell and at least one capture zone includes a cell-surface antigen-specific probe.

15. A method according to claim 14, wherein the determination is used to further determine a blood type.

16. A method according to claim 15, wherein the blood type includes determinations of more than three cell-surface antigens.

17. A method according to claim 16, wherein the blood type is a minor blood group type.

18. A method according to claim 14, wherein the probe is one of an antibody, an antibody fragment, a peptide ligand and an aptamer.

19. A method for determining the presence, absence, or quantity of multiple blood cell surface antigens in a blood sample of a patient, the method comprising:
   diluting a blood sample;
   contacting the diluted blood sample with first and second capture zones, the first zone functionalized to have a specific affinity for a first blood cell antigen and the second zone functionalized to have a specific affinity for a second blood cell antigen;

applying a first optical force having a dislodging component to at least one cell in the first zone, the first force being sized to be sufficient to dislodge a cell from the first zone if the first blood cell antigen is not present on the cell yet insufficient to dislodge a cell on which the first blood cell antigen is present;

applying a second optical force having a dislodging component to at least one cell in the second zone, the second force being sized to be sufficient to dislodge a cell from the second zone if the second blood cell antigen is not present on the cell yet insufficient to dislodge a cell on which the second blood cell antigen is present; and detecting dislodgement or non-dislodgment of the cells from the zones.

20. A apparatus for the analysis of the presence, absence or quantity of target moieties on one or more particles, the apparatus comprising:
    a substrate;
    a first and second capture zone disposed on the substrate, each capture zone comprising a plurality of probe moieties,
    wherein the avidity of the first and second capture zones are configured so that particles having a higher affinity to the capture zones will tend to be retained in the presence of a displacing optical force and particles having a lesser affinity for the capture zones will tend to be displaced in the presence of a displacing optical force, the optical force being in a specified range.

* * * * *